(12) United States Patent
Hancock

(10) Patent No.: US 9,351,713 B2
(45) Date of Patent: May 31, 2016

(54) NEEDLE STRUCTURE AND METHOD OF PERFORMING NEEDLE BIOPSIES

(71) Applicant: CREO MEDICAL LIMITED, Wales (GB)

(72) Inventor: Christopher Paul Hancock, Avon (GB)

(73) Assignee: CREO MEDICAL LIMITED, Chepstow (GB)

( * ) Notice: Subject to any disclaimer, the term of this patent is extended or adjusted under 35 U.S.C. 154(b) by 0 days.

(21) Appl. No.: 14/586,578

(22) Filed: Dec. 30, 2014

(65) Prior Publication Data
US 2015/0112190 A1    Apr. 23, 2015

Related U.S. Application Data

(63) Continuation of application No. 12/311,551, filed as application No. PCT/GB2007/003842 on Oct. 10, 2007, now Pat. No. 8,958,887.

(30) Foreign Application Priority Data

Oct. 10, 2006  (GB) .................................. 0620063.8

(51) Int. Cl.
*A61B 10/04*  (2006.01)
*A61B 10/02*  (2006.01)
(Continued)

(52) U.S. Cl.
CPC .................. *A61B 10/04* (2013.01); *A61B 1/018* (2013.01); *A61B 1/2676* (2013.01); *A61B 1/307* (2013.01);
(Continued)

(58) Field of Classification Search
CPC ........... A61B 10/0233; A61B 18/1477; A61B 18/18; A61B 18/1815; A61B 18/183; A61B 2018/00636; A61B 2018/00875; A61B 2018/00982; A61B 2018/1425; A61B 2018/183; A61B 2018/1869; A61B 2018/1876; A61B 2018/1892
See application file for complete search history.

(56) References Cited

U.S. PATENT DOCUMENTS

| 5,421,819 A | 6/1995 | Edwards et al. |
| 5,456,662 A | 10/1995 | Edwards et al. |

(Continued)

FOREIGN PATENT DOCUMENTS

| WO | WO 94/26186 A1 | 11/1994 |
| WO | WO 00/16697 A2 | 3/2000 |

(Continued)

OTHER PUBLICATIONS http://articles.mercola.com/sites/articles/archive/2005/04/16/needle¬biopsy.aspx "Are Needle Biopsies Safe"—internet article, Apr. 16, 2005.

(Continued)

*Primary Examiner* — Devin Henson
(74) *Attorney, Agent, or Firm* — Arent Fox LLP

(57) ABSTRACT

A biopsy needle having a longitudinal channel formed within an inner conductor of a coaxial antenna is disclosed. The coaxial antenna terminates in a rigid insertion tip e.g. a ceramic cone that is insertable into biological tissue. Microwave energy (e.g. having a frequency of 1 to 100 GHz) delivered to the coaxial antenna is emitted at the insertion tip. The insertion tip may be arranged to match the impedance of the coaxial antenna to a predetermined tissue impedance. The emitted radiation can be used to measure properties of or treat (e.g., ablate) tissue at the insertion tip. Needle biopsy apparatus is also disclosed, in which a microwave energy is controllably delivered to a needle from a microwave generator. The apparatus may include an impedance tuner to dynamically match the impedance of the needle with tissue at the insertion tip.

7 Claims, 18 Drawing Sheets

(51) Int. Cl.

| | |
|---|---|
| *A61B 1/018* | (2006.01) |
| *A61B 1/267* | (2006.01) |
| *A61B 1/307* | (2006.01) |
| *A61B 5/05* | (2006.01) |
| *A61B 5/06* | (2006.01) |
| *A61M 5/158* | (2006.01) |
| *A61N 5/02* | (2006.01) |
| *A61N 5/10* | (2006.01) |
| A61B 18/18 | (2006.01) |
| A61B 18/00 | (2006.01) |
| A61B 18/14 | (2006.01) |

(52) U.S. Cl.
CPC .............. *A61B 5/0507* (2013.01); *A61B 5/065* (2013.01); *A61B 10/0233* (2013.01); *A61B 18/18* (2013.01); *A61B 18/1815* (2013.01); *A61M 5/158* (2013.01); *A61N 5/022* (2013.01); *A61N 5/1007* (2013.01); *A61B 10/0283* (2013.01); *A61B 18/1477* (2013.01); *A61B 2010/045* (2013.01); *A61B 2018/00577* (2013.01); *A61B 2018/00636* (2013.01); *A61B 2018/00702* (2013.01); *A61B 2018/00875* (2013.01); *A61B 2018/00982* (2013.01); *A61B 2018/1425* (2013.01); *A61B 2018/183* (2013.01); *A61B 2018/1869* (2013.01); *A61B 2018/1876* (2013.01); *A61B 2018/1892* (2013.01); *A61N 2005/1024* (2013.01)

(56) References Cited

U.S. PATENT DOCUMENTS

| | | | |
|---|---|---|---|
| 5,693,082 | A | 12/1997 | Warner et al. |
| 6,261,241 | B1 | 7/2001 | Burbank et al. |
| 6,306,132 | B1 | 10/2001 | Moorman et al. |
| 6,325,796 | B1 | 12/2001 | Berube et al. |
| 6,355,033 | B1 | 3/2002 | Moorman et al. |
| 6,415,627 | B1 | 7/2002 | Pfister et al. |
| 6,582,427 | B1* | 6/2003 | Goble ............... A61B 18/042 606/34 |
| 6,770,070 | B1 | 8/2004 | Balbierz |
| 6,847,848 | B2* | 1/2005 | Sterzer ............... A61B 18/18 607/101 |
| 6,957,108 | B2 | 10/2005 | Turner et al. |
| 7,118,590 | B1 | 10/2006 | Cronin |
| 7,226,446 | B1* | 6/2007 | Mody ............... A61B 18/18 606/33 |
| 2003/0028094 | A1 | 2/2003 | Kumar et al. |
| 2003/0153908 | A1 | 8/2003 | Goble et al. |
| 2004/0097920 | A1 | 5/2004 | Desinger |
| 2004/0133254 | A1 | 7/2004 | Sterzer et al. |
| 2004/0243200 | A1* | 12/2004 | Turner ............... A61B 18/18 607/101 |
| 2006/0079774 | A1 | 4/2006 | Anderson |
| 2008/0275436 | A1* | 11/2008 | Cronin ............... A61B 18/18 606/33 |

FOREIGN PATENT DOCUMENTS

| | | |
|---|---|---|
| WO | WO 01/70114 A1 | 9/2001 |
| WO | WO 01/74252 A2 | 10/2001 |
| WO | WO 2004/037102 A1 | 5/2004 |
| WO | WO 2004/047659 A2 | 6/2004 |
| WO | WO 2005/115235 A1 | 12/2005 |

OTHER PUBLICATIONS http://www.g-mark.org/award/detail.html?id=31609&lang=en—"2005 Good Design Grand Award—press release", Jul. 2005.
Metcalfe, et al., "Useless and dangerous—fine needle aspiration of hepatic colorectal metastases" Br. Med. Jou., 328, pp. 507-508, Feb. 28, 2004.
Extended European Search Report of European Patent Application No. 15187994.7 dated Apr. 7, 2016.

* cited by examiner

NEEDLE STRUCTURE AND METHOD OF PERFORMING NEEDLE BIOPSIES

CROSS-REFERENCE TO RELATED APPLICATION

This application is a Continuation application of U.S. patent application Ser. No. 12/311,551, filed Oct. 23, 2009, which is a National Stage entry of International Application No. PCT/GB2007/003842 filed Oct. 10, 2007, which claims the benefit of priority of United Kingdom Application No. 0620063.8 filed Oct. 10, 2006. The disclosures of the prior applications are hereby incorporated in their entirety by reference.

TECHNICAL FIELD

The present invention relates to biopsy needles, i.e. needles adapted for the purpose of extracting fluid or cells (e.g. tissue) from the body e.g. for the purpose of identifying cancerous growths.

BACKGROUND TO THE INVENTION

A fine needle biopsy normally uses a thin hollow needle to remove a small tissue sample from an organ or a tumour. A common type of fine needle biopsy is a fine needle aspiration, where a fine needle and a syringe are used to remove either fluid from a cyst or clusters of cells from a solid mass. The procedure for fine needle aspiration and fine needle biopsy is basically the same, and the two procedures are sometimes performed together.

Fine needle biopsies can be obtained from organs or tumours located within the human anatomy. Common sites that may be considered for biopsy procedures to be performed include: breasts, kidneys, the liver, the pancreas, the prostate, the thyroid, lungs, ovaries and lymph nodes. Fine needle biopsy is a diagnostic tool used to evaluate organ or tumour tissue, and may also be used to establish whether or not certain treatments are working. It is normal for a local anaesthetic to be used to numb the area where the needle will be inserted. The thin hollow biopsy needle is inserted through the skin to the biopsy site. In current procedures, the needle may be inserted more than once for correct positioning or to obtain multiple samples.

When taking needle biopsies to identify potential breast tumours, it is normal practice for the surgeon to guide the biopsy needle into the area of concern by palpitating or feeling the lump, whenever this is physically possible, and then the needle may be located into the tumour based on this information. There is a high risk of false negatives occurring when taking biopsies in this manner, and it may be necessary to perform several needle biopsies in the region where the lump has been felt in order for there to be a good chance of locating the cancerous tissue.

If the lump is non-palpable, then the biopsy may be performed under image guidance, e.g. using ultrasound. However, even when ultrasound-guided needle biopsies are performed, it is normal to make several attempts at locating the cancerous site. Imaging using ionising radiation is also used to locate the biopsy needle inside the tumour. Fluoroscopy, where X-rays are directed onto a fluorescent plate, which is linked to a television camera, is used to see live images of the insertion of the biopsy needle on a monitor, and to establish the most appropriate position to take the biopsy. Computer tomography (CT) or computer aided tomography (CAT), where a scanner is used to rotate X-rays around the patient, is also used to guide the biopsy needle. This form of image guidance has the obvious drawback of exposing the patient to potentially harmful doses of X-ray radiation. Other drawbacks include: X-ray imaging procedures are expensive and can be time consuming, they require specialist support to drive the equipment, and they are not always successful in locating the cancerous site.

Needle biopsies are widely used and accepted as a safe and reliable test for the determination of the manifestation of cancer in the human body, but currently used methods may lead to cancerous cells being spread around the body when the biopsy needle is withdrawn. The concern is that during the procedure of removing the needle from the biopsy site, malignant cells may break away from the tumour and be deposited along the needle track that contains healthy tissue. This may lead to seeding and the development of new tumours. It has been reported[1] that a needle biopsy may increase the spread of cancer by 50% compared to patients who undergo lumpectomies.

[1] in an article by Dr Joseph Mercola (http://www.mercola.com/2005/apr/16/needle biopsy.htm)

Cases have been reported where the use of fine needle biopsies to diagnose liver tumours has led to metastases seeding along the biopsy needle track. In one clinical review[2] it is stated that the occurrence of seeding is likely to be the cause of the death of a particular individual described in the case study.

[2] Metcalfe M. S, Bridgewater F. B. G., Mullin E. J., and Maddern G. J., Br. Med. Jou., 328, 28 Feb. 2004, pp. 507-508

SUMMARY OF THE INVENTION

At its most general, the present invention proposes forming an antenna structure with the needle (hereinafter a 'needle antenna'), whereby the needle has the ability not only to perform conventional tissue extraction but also to couple microwave energy to and from the tissue to perform measurements and/or ablation of tissue e.g. at the needle tip.

The ability to measure dielectric properties of the tissue (the measured information) may offer significant advantage in terms of locating the cancerous tissue the first time the needle antenna is inserted into the region of tissue where it is suspected that a tumour is present, i.e. there may be no need to take a number of tissue samples. Also, the ability to measure tissue properties in this manner may reduce the risk of false negatives occurring.

The ability to measure information relating to the tissue at the exact location, where the end of the biopsy needle is located, may also offer significant advantage over location techniques that use the imaging (e.g. scanning) arrangements described above in that the scanning equipment may be unable to provide full or reliable details regarding the region where the tumour or cancerous tissue is located, due to certain biological structures obscuring the image, or due to image resolution or signal processing limitations. The present invention may not suffer from these limitations.

The seeding of new tumours caused by biopsy needles may be prevented by the ability to controllably ablate the needle track e.g. during withdrawal to kill any cancerous cells that would otherwise have been left behind. The present invention may be arranged to selectively perform both this ablation function and the measurement function.

Thus, the needle antenna disclosed herein may have the capability of directly measuring information relating to the tissue in the form of tissue type and/or the state of the tissue. The needle antenna described in this invention can also be used to perform controlled tissue ablation.

According to one aspect of the invention, there may be provided a biopsy needle insertable into tissue for introducing or extracting a sample therefrom, the needle having an elongate body terminating with an insertion tip, a longitudinal channel formed within the body for transporting the sample, and a coaxial antenna comprising an inner conductor and an outer conductor coaxial with the inner conductor and separated from it by a dielectric material, wherein the coaxial antenna is arranged to couple microwave energy to/from tissue at the insertion tip, and the channel is formed within the inner conductor or in an outer portion of the outer conductor. The inner conductor may be a conductive layer along an inside wall of the channel. Preferably, the inner conductor is a conductive layer (tube) that defines the channel. Preferably, the outer conductor comprises a conductive layer formed on the outer surface of the elongate body. The outer conductor may comprise a conductive layer formed on the dielectric material and an annular or part annular channel formed on that conductive layer. The coupled microwave energy may be selectable either to measure properties of tissue at the insertion tip or to ablate tissue at the tip.

In another aspect of the invention, there may be provided needle biopsy apparatus comprising a biopsy needle as described above and a microwave power source arranged to deliver microwave frequency energy to the coaxial antenna in the needle in order to measure and/or ablate tissue at the insertion tip of the needle. The apparatus may include a dynamic impedance tuner arranged to adjust the impedance of the needle e.g. to match the impedance of the tissue at the insertion tip in order to ensure even (uniform) energy delivery into the tissue. This aspect of the invention offers an advantage in that it enables uniform ablation of the channel through which the antenna is inserted to prevent the occurrence of seeding. The ability to dynamically match into various tissue structures prevents uneven ablation due to variations in matching to various tissue types as the tip of the antenna moves through the various structures.

In other words, the needle antenna described in this specification can couple microwave frequency energy into a coaxial structure for the purpose of making tissue type/state measurements, and/or for performing controlled tissue ablation, and has a hollow tube centre conductor to enable tissue biopsies to be performed before, after, or during the tissue ablation process. The structure disclosed in the current invention may, therefore, be considered as a tri-functional needle antenna. The frequency of choice used in the current invention, and the microwave aspects of the design of the tri-functional antenna structure makes it possible to measure information regarding the state of the biological tissue at the same location (position) as where the tissue biopsy is to be physically taken, i.e. at the distal tip.

In this specification, microwave frequency means a frequency range of between 1 GHz to 100 GHz, preferably 5 GHz to 60 GHz. Higher frequencies, e.g. up to 200 GHz may also be used. More preferably, the frequency source used operates at a frequency of between 14 GHz and 15 GHz, and, even more preferably, operates at a spot frequency of 14.5 GHz.

This invention may overcome problems associated with conventional needle biopsies and other similar tissue biopsy systems. The ability to perform tissue measurements and to controllably ablate tissue offers advantages in terms of preventing the seeding of cancerous cells, that is often associated with conventional needle biopsy procedures, by using controlled microwave energy to seal the track or channel made by the needle, allow fluid/tissue biopsies to be taken with a high degree of confidence that false negatives will not occur due to the ability of the system to distinguish between healthy and cancerous tissue by performing dielectric measurements at the tip of the needle using a low power microwave transceiver; it may be possible to eliminate the need to take multiple fluid/tissue samples as is often the case in current procedures (even when the needle is guided using ultrasound or X-ray imaging), where hitting the target only once out of several attempts is deemed to be sufficient to qualify as constituting a successful procedure. The current invention may also allow for biopsy samples to be taken before, after, and during ablation to help prevent loss of pathological information as occurs in normal percutaneous tumour ablation procedures using RF or microwave energy.

The tissue biopsy aspect of the current invention is not limited to the extraction of cancerous tissue, or for use in regions of the human body where cancerous tissue may exist.

It should be noted that the microwave design of the needle antenna structure described in this specification enables impedance mismatches at the distal tip of the needle antenna structure to be reflected back along the shaft of the antenna and the cable assembly attached thereto to the generator, where measurements of the reflected signal are used to calculate the requirements to enable the distal tip of the antenna to be matched to the generator, which may be a microwave power amplifier with an output impedance of 50 Ω.

It may also be desirable to use a dynamically adjustable tuning filter, for example, a waveguide cavity containing three tuning stubs with a spacing of a quarter of the guide wavelength at the frequency of interest, to create a conjugate match between the distal tip of the needle antenna and the load presented by the biological tissue structure. It should be understood that the tuning filter is positioned between the output from the power amplifier and the distal tip of the needle antenna to enable the output impedance of the amplifier to be matched to the input impedance of the tuning filter, and the output impedance of the tuning filter to be matched to the impedance of the biological tissue. This feature enables the needle antenna to be used to perform controlled ablation of a volume of cancerous tissue or to perform controlled ablation (or sealing) of the needle track (or channel).

The ability of the needle antenna to convey information back to the measurement system to allow dynamic impedance matching to be performed between the changing tissue impedance and the generator enables the energy delivered into the various tissue structures that exist along the track between the site where the tissue biopsy (or the tumour ablation) takes place and the outside world to be automatically regulated to provide uniform tissue ablation of healthy tissue structures en route, i.e. it may be desirable to ablate a channel of 4 mm diameter of healthy tissue along the track (or channel) to prevent the seeding of cancerous cells. The ability of the needle antenna structure to allow for the mode of operation described above to be performed may be an additional feature of the current invention.

The invention may also be used in the future for performing percutaneous musculoskeletal biopsies for helping clinicians diagnose benign or malignant musculoskeletal lesions due to the fact that the role of fine-needle aspiration in the diagnosis and management of musculoskeletal lesions is slowly gaining acceptance. It is also expected that cytopathology of bone and soft tissue tumours will serve to widen the usage of the fine needle aspiration technique.

The invention may also be used to perform biopsies of lung tissue. In this instance, depending on the exact location, a biopsy will be obtained either by a bronchoscopy or a needle biopsy. Needle biopsy is better for cancers near the periphery of the lungs (i.e. closer to the ribs than the centre of the chest), beyond the reach of the bronchoscope. In this procedure, the biopsy needle is inserted percutaneously through the chest wall to take a tissue sample.

The invention may not be limited to introducing the needle antenna percutaneously into the human body. The needle antenna described here may be introduced into the body by other means; examples include: through a trocar, through an endoscope, through a bronchoscope, through a natural orifice, through a cystoscope, or during an open surgical procedure.

The invention may not be limited to using a single frequency source for performing controlled ablation and making dielectric measurement. A plurality of frequency sources may be used. For example, it may be advantageous to use a lower microwave frequency, for example 1 GHz to 10 GHz, for performing controlled ablation, and a higher microwave frequency, for example, 20 GHz to 100 GHz, for performing dielectric measurements. The embodiments of the invention described below use a single frequency source operating at 14.5 GHz, which has the advantage of producing a high energy density for controlled ablation of small tumours and effective track (or channel) sealing, and a small enough radiation distance to allow for dielectric measurements that are localised to the end of the distal tip to be performed. The advantage of using lower microwave frequencies for tumour ablation is that the larger penetration depths associated with low frequency microwave energy may be beneficial in terms of producing effective ablation of large tumours, and the advantage of using higher microwave frequencies for dielectric measurement is that the small radiation distances associated with high frequency microwave energy may be beneficial in terms of effectively performing local tissue measurements that are unaffected by surrounding tissue structures.

From the above, it can be seen that this invention may be particularly useful in helping to promote the widespread use of needle biopsies. The ability to guide the needle to the exact location of the suspected tumour and the capability of being able to controllably ablate or seal the needle track to prevent seeding, may offer great advantage over existing biopsy and location techniques. The added ability of also being able to controllably ablate the tumour whilst performing a tissue biopsy may offer an extra advantage.

In another aspect, the present invention may provide a method of performing a needle biopsy comprising any or all of the following steps:

percutaneously inserting the biopsy needle antenna through healthy tissue to the cancerous site under the control of the tissue measurement system (i.e. performing the dielectric measurement), taking a first tissue (fluid or cell) sample, commencing controlled tumour ablation under the control of dynamic impedance matching, taking further tissue samples during the controlled ablation process (for example, the measurement interval may be 30 seconds), continuing ablation to achieve complete ablation of tumour and controlled ablation of an extra portion of healthy tissue to leave a safe margin, taking a final sample of tissue, sealing the needle track during needle withdrawal using the microwave energy source configured to a lower power setting, for example, between 2.5 W and 20 W, under the control of dynamic impedance matching to ensure that the various layers of tissue seen by the end of the needle antenna are ablated by the same amount and that this ablation process is well controlled.

The invention may be used to introduce material or treatment into the body e.g. during bracytherapy.

Materials introduced through the longitudinal channel e.g. at the centre of the inner conductor and/or in the outer portion (outer jacket) of the outer conductor may be used to augment the plume of ablation produced by the antenna or to adjust the shape of the plume. For example, a lossy material may be introduced or an additional electrode may be introduced that produces energy at a lower frequency where cable loss is of little significance.

A channel in the outer portion of the outer conductor may be used to circulate a coolant, for example saline or water.

In summary, the modes of operation of the current invention may be as follows:

1. Tissue biopsy and controlled track ablation to prevent seeding. Embodiments of the invention may provide the following advantages:

high microwave frequency and associated depth of penetration of energy ensures minimal damage to healthy tissue during channel ablation, and controlled solid state energy source ensures that the power delivered can be adjusted in accordance with tissue layer.

2. Tissue measurement (e.g. to recognise signature of cancerous tissue type) and tissue biopsy. Embodiments of the invention may provide the following advantages:

information from the measurement system can be used to ensure that tip of antenna is located at the centre of the tumour to reduce the risk of a false negative, and impedance measurement information can be used to complement the biopsy information.

3. Tissue measurement, tissue biopsy and controlled track ablation to prevent seeding. Embodiments of the invention may provide the following advantages:

measurement information gathered as antenna is withdrawn can be used in a feedback loop to control tissue impedance matching system to ensure that a uniform channel (around needle track) is ablated with minimal damage to healthy tissue, information gathered during pre-clinical studies regarding ablation plume shape and size can be used to ensure that no nodal information will be lost, ablation may be automatically started when (or prevented until) the tip of the antenna is located a predetermined distance from the node, impedance measurement information can be used to complement the biopsy information.

4. Tissue measurement and introduction of material into the body. Embodiments of the invention may provide the following advantages:

material can be introduced into the body using measurement system to locate the centre of the target tissue, introduced material can be used to augment the ablation process, i.e. by using a material that reacts with the microwave energy, a radioactive implant can be introduced accurately and the entrance channel can be controllably ablated to prevent seeding.

BRIEF DESCRIPTION OF THE DRAWINGS

Examples of the invention are discussed below with reference to the accompanying drawings, in which.

DETAILED DESCRIPTION; FURTHER OPTIONS AND PREFERENCES

Figure 1:
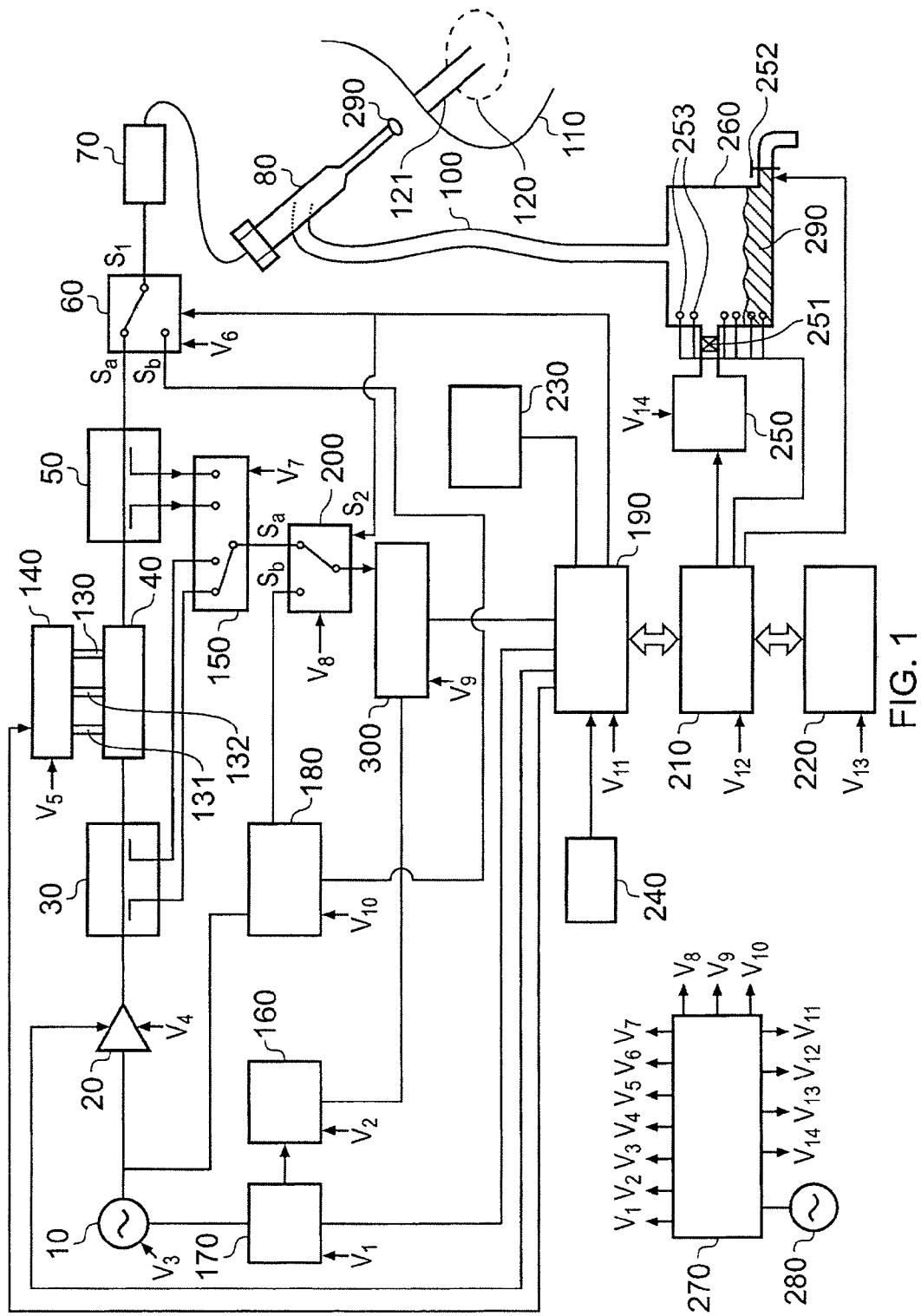
FIG. 1 is a block diagram of a needle biopsy apparatus that is a first embodiment of the invention.

In this description the term ablation may refer to the ablation of a region of cancerous tissue, for example a tumour, or for sealing a track or channel made as the needle antenna passes through layers of healthy tissue. The latter will generally require lower levels of power and the track ablation may be performed with dynamic energy matching to the tissue impedance seen en route to ensure that controlled amounts of energy is launched into the various tissue types as the needle antenna traverses through the tissue to the outside world. However this invention need not be limited to performing controlled ablation with dynamic impedance matching being in place.

In general terms, one embodiment of the needle antenna structure comprises a rigid stainless steel structure with an outside diameter of around 2.2 mm and a sharp ceramic pointed cone at the distal tip to enable percutaneous insertion. However, the invention need not be limited to this geometry or construction and may be realised using any suitable antenna structure that enables microwave energy to be transferred in the forward and reverse direction to enable the measurement of dielectric information, and to cause controlled tissue ablation, whilst allowing tissue samples (fluid or cells) to be extracted without upsetting the environment set-up to allow microwave signals to propagate for the purpose of making a dielectric measurement or for the purpose of introducing a high enough level of microwave energy into biological tissue to cause controlled tissue ablation.

The invention makes use of the fact that the centre conductor within the antenna is around 0.5 mm in diameter, but a wall thickness of about 0.01 mm only is required to enable almost all of the microwave energy to flow, or to be transported, along an appropriate conductive material when the frequency of operation is 14.5 GHz. Thus, in theory the centre of the centre conductor can be removed to leave a bore having a diameter of over 0.4 mm available as a channel that can be used to remove fluid from a cyst or cells within a solid mass. It is worthwhile noting that this channel could also be used to transport other liquids and/or solids in and out of the needle antenna. For example imaging or contrast media for specific tissue marking and/or identification.

It was recently reported that a Japanese scientist won a Good Design Award for the development of a 0.2 mm diameter needle for infusion, therefore, it can be the with confidence that the technology exists to enable the manufacture of a hollow centre conductor that suits these requirements.

For practical implementation in systems suitable for taking biopsies of breast tissue, the preferred hollow section for the needle centre conductor may be between 0.3 mm and 0.4 mm in diameter. This should provide enough mechanical strength, and ensure that all of the electromagnetic fields propagate along the outside of the centre conductor, i.e. the wall thickness is much greater than 0.01 mm, thus the electromagnetic fields set-up inside the structure would be unaware that the structure is hollow. To ensure that the overall needle antenna structure is rigid, and that it is allowed to be percutaneously inserted inside a patient, it is preferable to use stainless steel as the outer jacket of the needle antenna structure.

In this description, an antenna structure and apparatus is described that has the potential to perform the following functions:

measure dielectric information to determine the type, state and location of healthy and cancerous tissue, perform a needle biopsy with confidence that the tip of the needle is located inside the centre of the tumour, or other biological tissue that may require treatment, controllably ablate the tumour or other unhealthy tissue structures and a small region of healthy tissue (a safe margin), take further needle biopsies during and after the treatment process, and controllably ablate the channel made by the needle antenna during needle withdrawal to prevent seeding.

The new combined procedure involving tissue measurement, tissue biopsy, and tissue ablation can allow cancerous tissue (fluid or cells) to be located during a first attempt, and the risk of dragging cancerous cells back through the channel can be mitigated due to the fact that the needle channel (or track) is subjected to controlled ablation, thus causing the death of any cancerous cells that may be present at or around the distal tip of the needle antenna.

It should be noted that this device can be used to perform any combination of the above listed functions, for example, it could be used to locate the needle antenna into the centre of the tumour and take the biopsy, or it could be used to take the biopsy and seal up, or controllably ablate, the channel to prevent the risk of seeding; it could be used to take the biopsy, ablate the cancerous tumour and then seal the channel, or it may be possible to take a tissue biopsy before, during and after tissue ablation has taken place to ensure that the tumour has been successfully destroyed using thermal ablation.

It may also be desirable to use the current invention to deposit materials into the biological system rather than removing tissue from the biological system. In this mode of operation, the tissue measurement and characterisation feature may be used to identify the region of the body where a material (solid or liquid) is required to be located with a high degree of accuracy, and the material may be deposited at the exact desired location (features associated with the use of the low power microwave frequency transceiver facilitates this). This aspect of the current invention may be particularly useful for depositing a particular drug or a radioactive dye into the body for example. This idea may be used with brachytherapy. The ability to target the exact location where a drug is to be delivered may offer significant advantage in terms of minimising the concentration and amount of drug required.

It should also be noted that the centre tube may be used to suck out or remove ablated tissue in order to increase the zone of ablation. This may be of particular use where the ablated tissue has become charred. Once the tissue has been removed the ablation process may commence again and the process repeated a number of times. Since it is not only the centre of the centre conductor that is transparent to the microwave field, but also the outer of the outer conductor may also be hollow, it is possible to use this as a second channel for taking the biopsy and for removing tissue.

This invention is not limited to removing fluid or cells associated with cancerous tumours; the needle antenna may be used to remove other tissue from sensitive regions of the body where it is required to accurately locate the biopsy tissue inside target tissue. In these applications, the invention may be operated in measurement mode only.

The tri-functional nature of embodiments discussed herein may be particularly useful for performing biopsies on underarm lymph nodes, in which the presence or absence of breast cancer cells is a powerful predictor of whether the cancer has spread. It is now possible to examine such biopsies to help decide appropriate therapy for metastatic breast cancer without the need to remove a sentinel lymph node for examination under a microscope. The biopsy method is much quicker and less invasive than the surgical procedure. The present invention can make the biopsy method more accurate and controlled.

The present invention permits accurate location of the lymph node using the measurement mode, extraction of tissue for examination through the biopsy channel, and controlled ablation to seal the needle track during withdrawal using the ablation mode. To avoid damaging the lymph node (e.g. by ablation), the measurement mode may be used to determine when the tip of the probe leaves the node. By leaving the node intact, it can be used for further measurement in future. The size of the ablation plume (e.g. extent of high power microwave radiation field) produced by the needle is repeatable and well defined for a given power level and pulse profile. Accordingly, in combination with the measurement mode it is possible to accurately and repeatably insert a safety zone e.g. of 1-5 mm between a measurement position (e.g. lymph node) and the start of ablation (e.g. higher power mode (e.g. 10 W) to seal the needle track and prevent seeding of cancer cells). The ablation mode may be automatically enabled based on information obtained in the measurement mode.

Moreover, if the embodiment includes a tuner for implementing the dynamic impedance matching discussed above, evenly ablation of the needle track during withdrawal can be achieved even when that track passes through different tissue types i.e. materials having different conductivities and permittivities at the frequency of interest.

A further feature of the current invention may be to pump water or saline through the biopsy channel during ablation to keep the needle antenna as cool as possible. It may be advantageous to use this feature in applications where it is desirable to treat large lesions. In this instance, it may be required for the level of microwave power to be increased from that used when operating in the treatment mode under normal conditions, for example, where spherical tumours of diameter greater than 2 cm are to be treated, or where it is required to deliver power over longer durations of time. For example it may be required to generate up to 100 W of continuous wave (CW) power for ten minutes in order to treat a spherical lesion of, for example, 10 cm in diameter.

Alternatively, the biopsy may be used to introduce a material (e.g. lossy biocompatible material) which can augment the ablation effect, e.g. increase the ablation volume that is achievable with the apparatus. The presence of the material within the needle may not affect the generated microwave field because the microwave energy only flows in the outer section of the inner conductor.

The method and device used to either collect tissue (or other substances) from the human body, or to introduce substances into the human body, through a channel contained within the needle antenna introduced here, will be determined by the specific application of the current invention. In most procedures, a syringe may be used but this invention is not limited to using a syringe.

In one embodiment, the biopsy channel may be used to suck necrosed or charred tissue from the needle tip during ablation. This may be particularly beneficial where dynamic impedance matching is implemented because it removes the charred tissue that the needle would otherwise have to be matched with. Typically charred tissue presents a load that is very different from that which the needle may be designed to match with in the absence of a tuner.

In another embodiment, the device may be used in liposuction. The delivered microwave radiation may be used to heat fat which can then be sucked out via the biopsy channel. When used with a dynamic impedance matching apparatus, the needle impedance can be matched to the impedance of fat to target the heating. This apparatus may reduce the invasive nature of liposuction and facilitate its use on fine tissue structures or in cosmetic surgery, where it is desirable to minimise scarring or other permanent damage. Moreover, the configuration of the channel may act to concentrate the microwave energy around the channel, which can be beneficial in targeting heating at the location where it is required.

In the following full description of the current invention, certain aspects relating to apparatus, or electronic instrumentation, for producing controlled tissue ablation, and apparatus for detecting changes in tissue state is given as an overview only, since the inventor's earlier applications WO 2004/047659 and WO 2005/115235 describe these aspects in detail. On the other hand, it should be noted that the current description does address particular aspects of a sensitive measurement transceiver (for measurement mode) and the operation of the matching filter (for controlled ablation mode).

Skin Effect & Needle Antenna Dimensions

This invention makes use of the fact that as the frequency of the energy increases, conduction begins to move from an equal distribution over the entire cross section of a conductor to only existing at the surface of the conductor. Microwave frequencies in the super high frequency band (SHF), e.g. where the frequency is greater than 3 GHz, are preferably in the invention since these lend themselves particularly well where it is desirable for the thickness of the conductor to be less than 0.1 mm, or more preferably less than 0.01 mm. The preferred frequency used in the current invention is 14.5 GHz and the conductor preferably has a high conductivity, thus enabling conductor thicknesses to be in the micrometer (μm) region. The phenomenon associated with the reduction in conductor thickness as the frequency of the electromagnetic energy increases, is known as the skin effect.

The use of high microwave frequency radiation, i.e. radiation from a source operating at a frequency above 10 GHz, is advantageous in that the microwave energy produces a low propagation distance or depth of penetration inside the tissue, hence the dielectric measurement is localised to the end of the needle antenna where the fluid or cells are extracted from the biological system. It should be clear from the above that the current invention will enable the point where the dielectric (or tissue type/state) measurement is taken to be the same as where the tissue biopsy is extracted. It should also be understood from this statement that it is advantageous to design the tip of the needle antenna to be sensitive to changes in tissue impedance. For example, the material used at the distal tip of the needle antenna preferably exhibits a low dissipation factor at the frequency of interest, and the relative permittivity of this material may be chosen to provide a good impedance match between a representative tissue impedance and the impedance of the rest of the needle antenna structure. It should be noted that the tissue impedance is a function of the relative permittivity and the conductivity of the tissue at the frequency of interest. These two parameters can be used to describe the behaviour of dielectric materials at microwave frequencies.

When current is flowing through a conductor, the magnetic flux that results is in the form of concentric circles. Some of the flux exists within the conductor and links more strongly with the current in the centre. The result is that the inductance of the central part of the conductor is greater than the inductance of the conductor near the surface. This is because of the greater number of flux linkages existing in the central region. At high frequencies the reactance of the extra inductance is sufficiently large to enable the current to flow along the surface of the conductor where the impedance is low rather than near the centre of the conductor where the impedance is high.

Depending on the bulk resistivity of the conductor, at sufficiently high frequency all of the microwave current will flow within a very small thickness of conductor. Also, the current tends to concentrate nearest to the surface that abuts the highest relative permittivity. The use of materials with low bulk resistivity leads to shallower skin depths.

Figure 6:
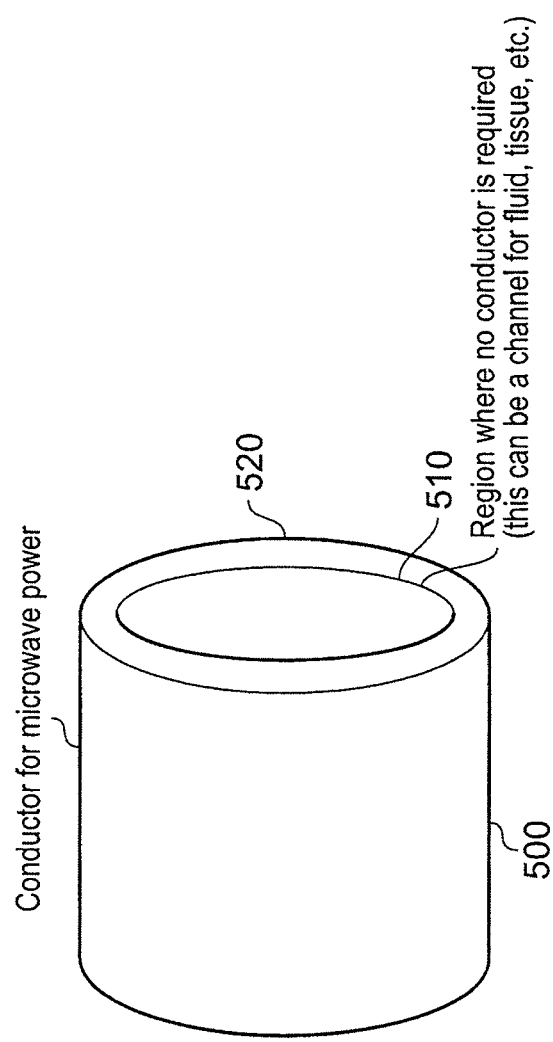
FIG. 6 is a diagram illustrating the skin effect.

For a solid wire, the current concentrates on the outer surface. For this reason, when skin depth is shallow, the solid conductor can be replaced by a hollow tube with no loss in performance. This phenomenon is illustrated in FIG. 6. Skin depth can be calculated using either equation 1 or equation 2:

$$\delta_s = \sqrt{\frac{2}{\omega\mu\sigma}} \qquad 1$$

$$\delta_s = \sqrt{\frac{\rho}{\pi\mu f}}, \qquad 2$$

where $\delta_s$ is skin depth in meters (m), ω is radian frequency (2πf) in Hertz (Hz), σ is conductivity in siemens (S or Ω/m), ρ is resistivity in ohms meters (Ωm), f is frequency in Hertz (Hz), and μ is permeability of free space in Henry per meter (H/m) (=4π×10$^{-7}$ H/m).

Table 1 provides values of skin depth at spot frequencies of 1 MHz, 10 MHz, 100 MHz, 1 GHz and 10 GHz for commonly used conductive materials. This table illustrates the need for using high microwave frequencies in small diameter structures when metallisation thickness is to be kept to a minimum, for example, in a co-axial arrangement where a hollow centre conductor with the largest diameter biopsy channel is required.

TABLE 1

Skin depth (in μm) for various commonly used materials at frequencies of 1 MHz, 10 MHz, 100 MHz, 1 GHz and 10 GHz

| Material | Symbol | Bulk Resistivity at 20° C. (Ω × 10$^{-8}$ m) | Skin Depth (μm at frequency) | | | | |
|---|---|---|---|---|---|---|---|
| | | | 1 MHz | 10 MHz | 100 MHz | 1 GHz | 10 GHz |
| Aluminium | Al | 2.65 | 81.9 | 25.9 | 8.19 | 2.59 | 0.819 |
| Beryllium | Be | 3.3 | 91.4 | 28.9 | 9.14 | 2.89 | 0.914 |
| Brass | Cu70/Zn30 | 7 | 133 | 42.1 | 13.3 | 4.21 | 1.33 |
| Bronze | Cu89/Snll | 15 | 195 | 61.6 | 19.5 | 6.16 | 1.95 |
| Copper | Cu | 1.69 | 65.4 | 20.7 | 6.54 | 2.07 | 0.654 |
| Gold | Au | 2.2 | 74.7 | 23.6 | 7.47 | 2.36 | 0.747 |
| Graphite | C | 783.7 | 1409 | 446 | 141 | 44.6 | 14.1 |
| Nickel | Ni | 6.9 | 132 | 41.8 | 13.2 | 4.18 | 1.32 |
| Silver | Ag | 1.63 | 64.3 | 20.3 | 6.43 | 2.03 | 0.643 |

The percentage of power transferred as a function of material thickness can be described by equation 3

$$\% P = (1 - e^{-x/\delta_s}) \times 100, \qquad 3$$

where x is the thickness of the layer of metallisation in meters (m), and % P is percentage of the power flowing in given thickness of metallisation in watts (W). For example, equation 3 predicts that for a thickness of metallisation of six skin depths, 99.75% of the power will be transported.

Figure 7:
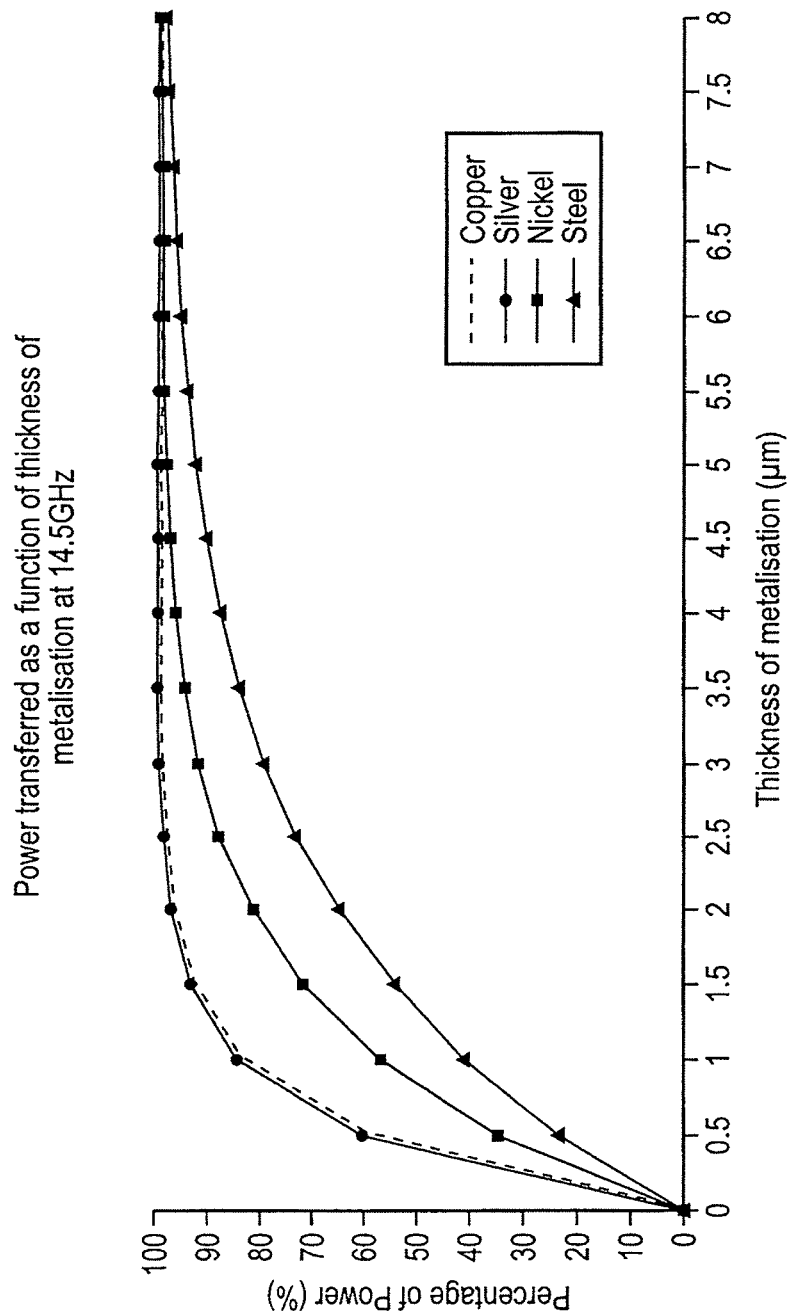
FIG. 7 is a graph representing the amount of power transferred using an energy source operating at a frequency of 14.5 GHz as a function of metal layer thickness for various metals.

In the embodiments described below, four commonly used metallic materials were considered. These were: copper, silver, nickel, and steel. FIG. 7 shows, the variation of power transported as a function of metallisation thickness for these four materials based on skin depth calculations using equation 1, and the exponential relationship given in equation 3. For the generation of FIG. 7, the frequency of operation used was 14.5 GHz, it is assumed that the materials are non-magnetic, and the following conductivity values (σ) apply:

Silver: σ=5.80×10⁷ S/m

Copper: σ=6.14×10⁷ S/m

Nickel: σ=1.28×10⁶ S/m

Steel: σ=5.0×10⁶ S/m

It can be seen that the best material to use in order to minimise the thickness of metallisation is silver. This if followed very closely by copper. The thickest layer of metallisation is required when using steel. It should be noted that the line for steel does not converge with the other three materials on the graph shown in FIG. 7, where the maximum thickness shown is 8 μm.

Table 2 provides figures for the required thickness of metallisation for 90%, 99% and 99.9% of power flow for silver, copper, nickel and steel:

TABLE 2

Thickness of metallization requirements for commonly used conductors when the operating frequency is 14.5 GHz

| Power transferred (%) | Silver | Copper | Nickel | Steel |
|---|---|---|---|---|
| | Thickness of metallization (μm) | | | |
| 90 | 1.23 | 1.26 | 2.69 | 4.30 |
| 99 | 2.46 | 2.53 | 5.38 | 8.61 |
| 99.9 | 3.68 | 3.79 | 8.07 | 12.91 |

It should be noted that the ability to minimise the thickness of the metallisation layer leads to the ability to fabricate needle antenna structures with minimal inside and outside conductor diameter thicknesses. This has the advantage of minimising the outside diameter of the needle antenna structure and/or maximising the diameter of the biopsy channel (this analysis assumes that it is required to keep the characteristic impedance of the structure constant and that the relative permittivity of the dielectric material between the inner and outer conductors is constant. These features may be advantageous where percutaneous systems are used to perform tissue ablation and/or dielectric (tissue state/type) measurement and for taking tissue biopsies.

The characteristic impedance of the co-axial needle antenna structure is described by equation 4 given below:

$$Z_0 = \frac{138}{\sqrt{\varepsilon_r}} \log_{10} \frac{c}{e}, \qquad 4$$

where $Z_o$ is the characteristic impedance of the co-axial line in ohms (Ω), $\varepsilon_r$ is the relative permittivity of the dielectric material between the centre conductor and the outer conductor, c is the inner diameter of outer conductor in meters (m) and e is the outer diameter of inner conductor in meters (m). The location of diameters c and e are illustrated on the tri-functional needle antenna structure shown in FIG. 8.

Figure 8:
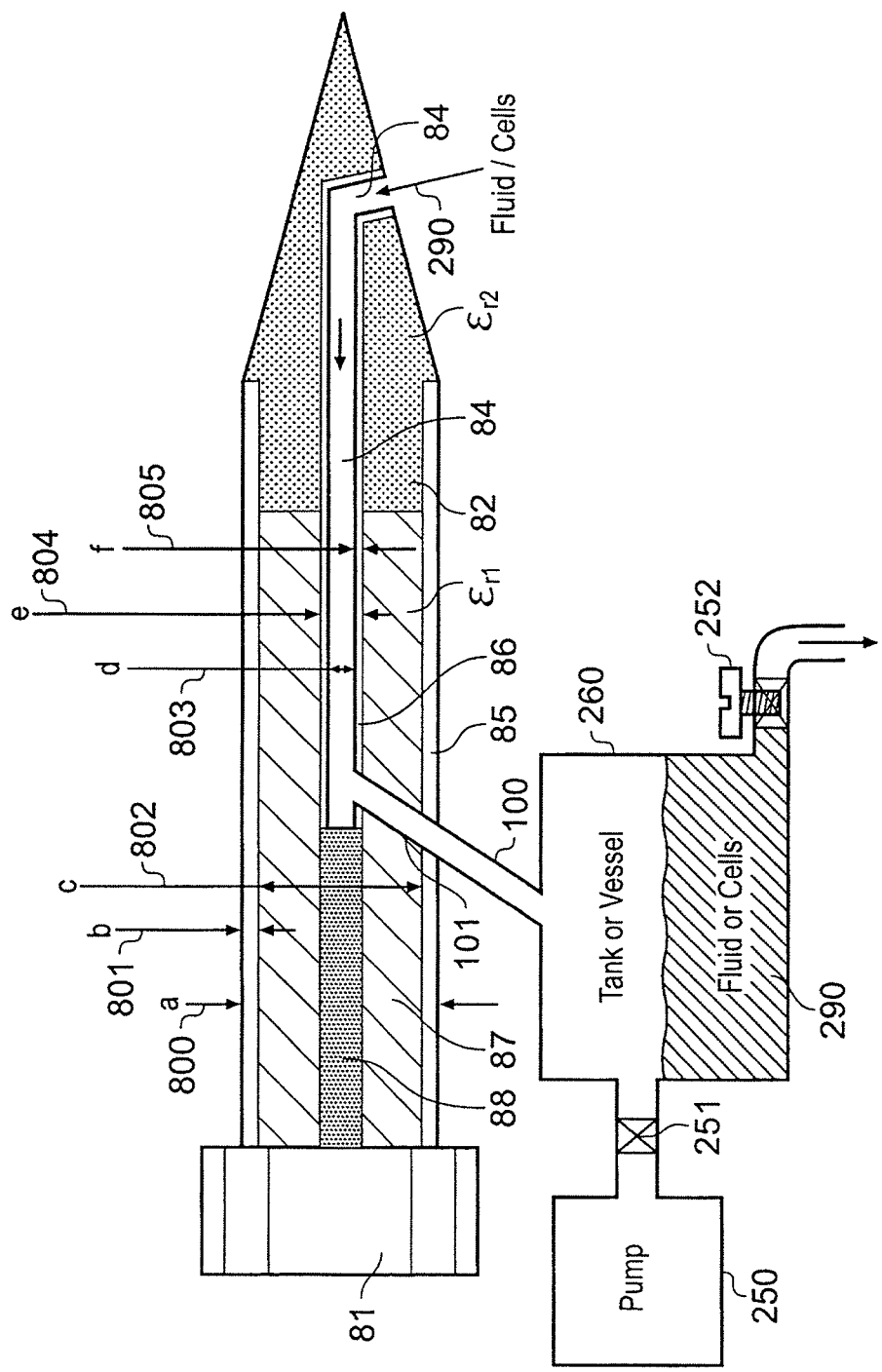
FIG. 8 shows a needle antenna that is a fifth embodiment of the invention.

Referring to FIG. 8, in a structure that uses steel as the metallic material, has a dielectric filling between the two conductors with a relative permittivity of 3.045, operates at a frequency of 14.5 GHz, and has a characteristic impedance of 50Ω, the following physical dimensions (calculated using equations 1, 3 and 4) may be used:
thickness b of steel for 99.9% of the energy to be transported=12.91 μm
outer diameter of needle antenna a=2.2 mm
inner diameter of outer conductor c=2.18 mm
outer diameter of inner conductor e=0.51 mm
inner diameter of inner conductor d=0.49 mm This is an illustrative example that enables a biopsy channel with a diameter of up to 0.49 mm (in theory up to 0.49709 mm) to be used. This example assumes that the dielectric material used is a had rod of material with a hole of 0.51 mm diameter bored through the centre. It would be necessary for a first layer of steel of thickness 12.91 μm to be deposited onto the outside of the rod, and a second layer of steel of thickness 12.91 μm to be deposited onto the inside wall of the hole bored through the centre of the rod.

The idea of taking a hard dielectric and coating the outer surface and the inner wall of the centre hole may be an independent aspect of the invention.

The idea of limiting the coating thickness of the metallisation attached to the wall on the inside bore hole to a thickness whereby it is considered that all the energy will flow, but no greater than this, i.e. in this case 12.91 μm, enables the diameter of the biopsy channel to be maximised and allows the maximum amount of tissue to be transported along the biopsy channel.

In the example given here, steel has been used because it exhibits the lowest conductivity out of the four materials considered as possible candidates for this work.

Biopsy Apparatus

FIG. 1 shows a block diagram of the overall system. This configuration enables all three modes of operation to be performed using a single needle antenna structure 80. In the dielectric measurement (or tissue recognition or location mode), stable frequency source 10 is used as the low power transmitter signal and is fed into the low power transmitter circuit 180, where it is channeled into needle antenna 80 through mode select switch 60, and cable assembly 70. The measurement signal, taken with needle antenna 80 inserted into biological tissue 110 to the area of concern 120, is then fed back into receiver 300 via cable assembly 70, mode select switch 60, low power measurement transmitter 180 (containing high isolation circulator with a carrier cancellation circuit), channel select switch 200, and into receiver 300. Receiver 300 uses local oscillator 160 to produce a first intermediate frequency (IF) signal that is used to convert the measurement signal into a form that enables digital signal processor 190 to extract both magnitude and phase information from the signal. Receiver 300 may contain a second IF stage (this is not shown in FIG. 1). The phase and magnitude information is then processed using digital signal processor 190 and/or microprocessor 210 to determine the type of tissue 290 that the tip of needle antenna 80 is in contact with. The tissue type 290 may be displayed using the user interface 220.

In the controlled ablation mode, stable frequency source 10 is fed into power amplifier and control sub-system 20, which is used to control the level and the duration of the power being delivered (the energy profile) into target tissue 120 to enable controlled ablation to be performed, or into the needle channel 121 for controlled sealing of the track. The output from power amplifier and control unit 20 is fed into first forward and reflected power coupler unit 30, whose function is to measure a portion of the forward power coming out of power amplifier 20 and the power reflected back due to a mismatch at the input of matching filter 40. The portions of forward and reflected powers are fed into the inputs to monitor select switch 150. The output from first forward and reflected power coupler unit 30 is fed into the input of matching filter 40, whose function is to impedance match power source 20 to load impedance seen by the distal tip of needle antenna 80, which may be either the treatment tissue 120, or the needle track 121. The tuning of matching filter 40 is performed by moving three tuning stubs 130, 131, 132 in and out of a waveguide cavity that forms a part of the matching filter 40. The movement of stubs 130, 131, 132 is performed using stub-actuator and a suitable control unit 140. It may be preferable to use linear actuators and a proportional-integral-differential (PID) control system (not shown here). The output from matching filter 40 is fed into a second forward and reflected power coupler unit 50, whose function is to measure a portion of the forward power coming out of matching filter 40 and the power reflected back due to a mismatch at the distal tip of needle antenna 80. The portions of forward and reflected powers are fed into the inputs to monitor select switch 150.

The position of stubs 130, 131, 132 is determined by the signals at the coupled ports of first and second forward and reflected power couplers 30 and 50 respectively. These signals are measured by polling each of the four switch positions of monitor select switch 150. The switch position is determined by a select signal provided by digital signal processor 190. The single output from monitor select switch 150 is fed into receiver 300 via channel select switch 200, where the switch contact connects the monitor select switch 150 to the input to receiver 300. The receiver 300 has an internal frequency mixer (not shown) that uses the selected signal from first and second forward and reflected power couplers 30 and 50 respectively and the local oscillator signal 160 to produce a first IF frequency. A second internal frequency mixer is used to form a second IF stage (not shown) and the output signal from the second IF stage is fed into digital signal processor 190, where phase and magnitude extraction is performed. The digital signal processor 190 uses the phase and magnitude information to determine the required signals to send to stub actuator and control unit 140 to enable tuning stubs 130,131, 132 to be moved inside the waveguide of matching filter 40 to positions whereby the output from power amplifier 20 is matched to the impedance seen at the distal tip of needle antenna 80. The output from second forward and reflected power coupler 50 is connected to mode channel switch 60, which is configured to connect the output from the forward and reflected power coupler 50 to the input to cable assemble 70. The output of cable assembly 70 is connected to the input, or the proximal end, of needle antenna 80. A control signal from digital signal processor 190 is used to change the switch contacts within channel select switch 200 and the mode select switch 60 to enable the controlled ablation mode or the tissue measurement mode to be selected.

It has been assumed here that the digital signal processor 190 contains an analogue to digital converter (ADC) to convert the analogue signals from receiver 300 into a digital format. In practice, it may be preferable to use an external ADC unit. A footswitch 240 is used to activate tissue ablation and measurement. The microwave energy output from the generator 60 and the input line from footswitch 240 contain DC isolation barriers (not shown here); these are required to prevent the generator from being connected to the user or patient circuit via a DC path (not shown here). In the ablation mode, the user interface 220 may indicate the energy dosage delivered into the tissue, the treatment time, and any other useful and/or relevant information. In biopsy mode, it may be desirable for user interface 220 to show the level of tissue contained in vessel 290 and when pump 250 has been activated. In tissue measurement mode, it may be desirable for user interface 220 to show display tissue type and/or tissue state. It may also be desirable to sound an audible alarm or flash the display when the distal tip of the antenna comes into contact with cancerous tissue.

Stable frequency source 10 and local oscillator 160 use the same temperature compensated stable crystal oscillator 170 as a reference source. The reference may also be fed into digital signal processor 190 and may be used as a timing reference.

Before the commencement of tissue measurement, or dynamic controlled ablation, it is necessary to calibrate needle antenna 80 using needle antenna calibration unit 230. Calibration is performed by inserting needle antenna 80 inside a cavity, or slot, contained within needle antenna calibration unit 230 (the cavity or slot may be co-axial or waveguide). A control signal from digital signal processor 190 is used to actuate a linear motor contained within calibration unit 230 to move a sliding short along a waveguide cavity to enable a number of calibration points to be measured. During calibration, the proximal end of cable assembly 70 must be connected to the RF output port of the microwave generator 60, and distal end of cable assembly 70 must be connected to the proximal end of needle antenna 80. It should be noted that it may be preferable to integrate cable assembly 70 and needle antenna 80 into one assembly during the device manufacturing stage.

Mode select switch 60 and channel select switch 200 are configured in such a way that they change contact position at the same time; these two switches enable controlled ablation or measurement mode to be selected. The position control comes from a select signal provided by digital signal processor 190. In the first switch position ($S_a$) the system is operated in ablation mode, and in the second position ($S_b$) the system is operated in measurement or tissue recognition mode.

A fluid feed pipe 100 is connected to needle antenna 80, preferably through a side wall of needle antenna 80, and fluid feed pipe 100 connects to a collection tank or vessel 260, which is used to collect biopsy tissue (fluid or cells) 290. An internal pipe connects the outer jacket of needle antenna 80 to the centre conductor of needle antenna 80 (not shown here). A pump 250 is used to suck the tissue sample 290 along a hollow channel contained within needle antenna 80 (not shown here), and suck the tissue through tissue feed pipe 100 into tank 260. It must be ensured that there are no leaks in the system. A valve 251 is used to ensure that tissue 290 cannot be directed into pump 250. Microprocessor 210 is used to control the operation of pump 250. It may be desirable to attach fluid level monitors or sensors 253 inside tissue vessel 260 to monitor the level of tissue inside the vessel; microprocessor 210 may be used to process signals from level monitors or sensors 253 and this information may be displayed using user interface 220. Microprocessor 210 may also be used to control the operation of valve 252, which is used to empty vessel 260. The operation of valve 252 may be based on information obtained from level sensors 253. It should be noted that tank 253 and pump 250 may be replaced by a syringe.

Cable assembly 70 is preferably a low loss coaxial cable with low random phase variation with flexure, but other cable assemblies, such as flexible waveguide, may be used. It is preferable for the insertion loss of the cable to be less than 1 dB per meter and for the random phase variation with flexure to be less than 1° rms.

DC power supply 270 is used to supply the sub-assemblies and units with DC, power.

It may be preferable to apply a conformal coating of Parylene C material to the needle antenna structure. A coating thickness of around 10 μm will not affect the microwave behaviour of the structure but will reduce the coefficient of friction on the needle surface and help reduce friction between the needle antenna and the tissue as the needle antenna is pushed through various types of tissue. Parylene C is easy to apply and is a biocompatible material that has undergone extensive material tests concerning its use inside the human body. Should the tip of the tri-functional needle antenna be made from a non-biocompatible material, the inclusion of a layer (or coating) of Parylene C may enable the structure to be used inside the human body.

It must be ensured that the fluid pumping system is a sealed system and that no fluid or tissue is able to leak in the region of the pipe that connects the centre conductor and the outer conductor. In the instance where a ceramic cone tip is used and the fluid is fed through the ceramic tip, it must be ensured that the interface between the hollow ceramic section and the centre conductor is sealed. It may be desirable to extend the centre conductor to the end of the ceramic cone tip. Full electromagnetic field analysis is performed on the new structure to take into account discontinuities and to ensure that the microwave operation of the structure is not in any way impaired.

It should be pointed out that if leaks exist in the system then it may be difficult to pump tissue or fluid from the sample site 120 to the tank or vessel 260. If there are leakage points then air will get into the system, which may make it more difficult, to transport tissue from the cancerous site 120 to the tank or vessel 260. It may be desirable to remove any air bubbles that may occur in the system before pumping fluid from the body.

Figure 2:
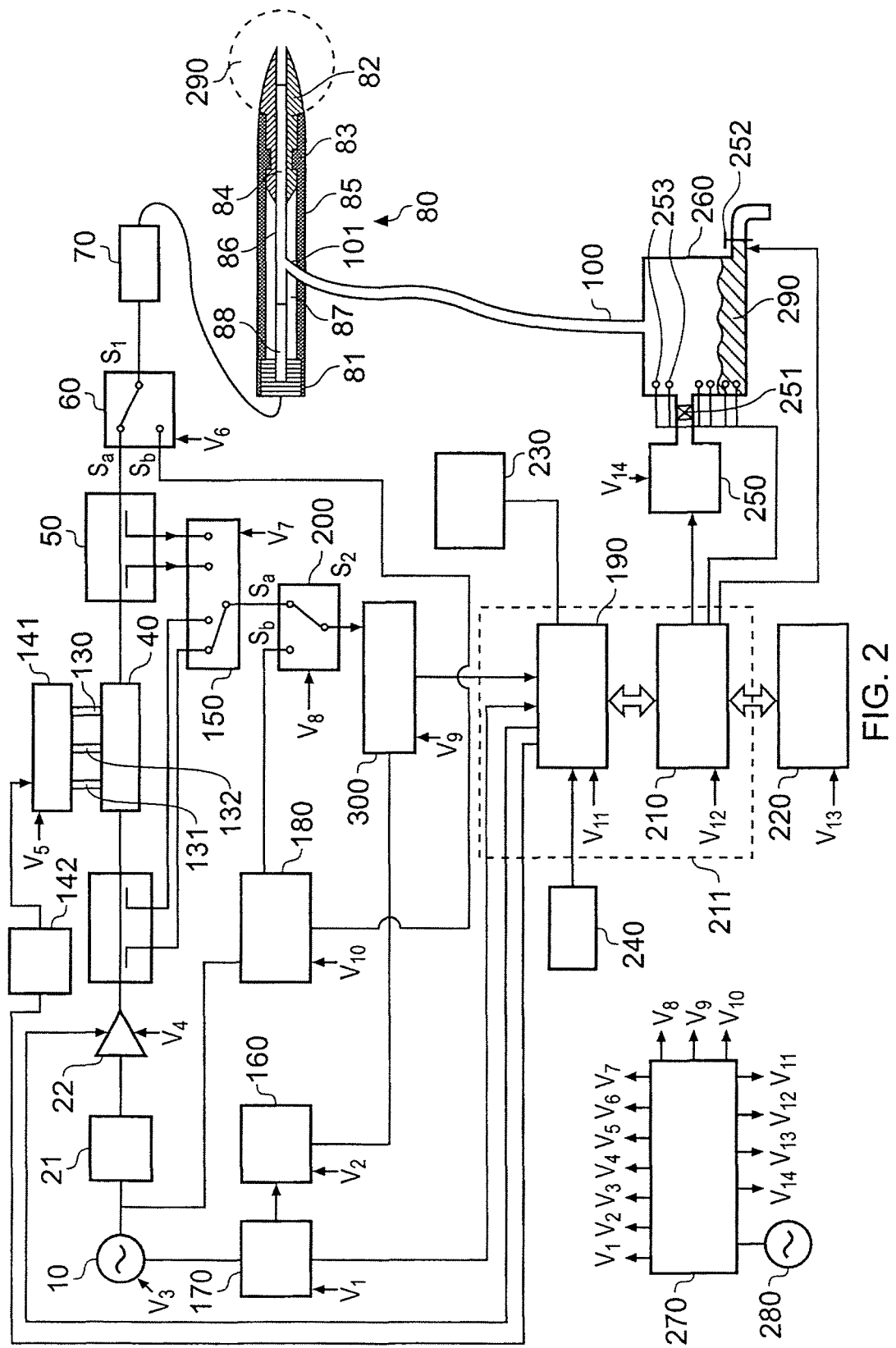
FIG. 2 is a more detailed diagram of the apparatus shown in FIG. 1.

FIG. 2 shows a block diagram of the complete system, where the construction of needle antenna 80 is shown in detail. It should be noted that the functionality of FIG. 2 is identical to that of FIG. 1, which has already been described in detail above. Physically, other than details of needle antenna 80, FIG. 2 is identical to FIG. 1, except for the following differences in component or sub-assembly partitioning: In FIG. 2, power amplifier and control unit 20 has been split up into two units, namely: power/modulation control unit 21, and power amplifier 22, stub actuator and control unit 140 has been split up into: linear actuators 141 and actuator controller 142; and microprocessor 210 and digital signal processor 190 has been combined into microprocessor and signal processor 211.

Needle antenna 80 comprises an input microwave connector 81, which may be any suitable microwave connector that can be used at the microwave frequency that is of interest for use in the current invention, for example: SMA, MCX, or SMC types. The microwave connector 81 is used to connect the needle antenna 80 to the cable assembly 70 and is also used to couple microwave energy into and out of the needle antenna 80. The proximal end of the centre conductor 88 is connected to the centre conductor of microwave connector 81. It may be preferable for the first section of centre conductor 88 to be a solid conductor up until a connection is made between the centre conductor 88 and connection pipe 101, which attaches to the tissue transport tube 100. Centre conductor 88 is hollow from the interface between tissue connection pipe 101 and centre conductor 88 to the distal tip of the needle antenna structure 80, where tissue 290 is sucked into centre conductor 88. The hollow section 84 has a diameter such that the wall thickness 89 between the solid section and the distal tip of centre conductor 88 is such that the transport of microwave energy is unaffected by the removal of the centre section of the centre conductor, and the wall of conductor 89 has enough strength to support itself and to allow for the needle antenna structure to be assembled with ease when the instrument is manufactured. It is preferable for the thickness of the wall of centre conductor 88 to be at least six skin depths in thickness in order to ensure that most of the microwave energy is transferred. The skin depth is determined by the properties of the material and the frequency of operation; full details of skin depth characteristics and calculations of skin depth for suitable materials have already been given in this description. A connection pipe 101 connects the hollow region 84 of centre conductor 88 to the tissue transport tube 100, which is attached to collection vessel 260. The pipe 101 may be made from a dielectric material or a conductor. It is preferable for pipe 101 to be made from a similar material to that of first dielectric material 87 in order to preserve the characteristic impedance of the co-axial structure and to minimise discontinuities within the structure. The location, size and the material used for pipe 101 may affect the transverse electromagnetic (TEM) fields set up in the co-axial structure, but any changes to the field distribution may be compensated for by including a matching transformer inside the structure near pipe 101; the matching transformer may be a tuning stub, which may be a conductive pin or a dielectric post. If a means of matching out the effect of the connection pipe 101 is required, then the matching structure may simply be a change in relative permittivity of dielectric material 87 or an additional pin inserted through the wall of the outer conductor 85 in the region of connection pipe 101. The specific embodiment of the matching structure will be dependent upon the specific geometry of the needle antenna structure 80 and it may be necessary to perform an electromagnetic field simulation of the complete needle antenna to determine the best matching structure to use. It should be noted that for small feed channels 84 and small connection pipes 101, the field discontinuity produced by including the connection pipe 101 into the structure will be negligible and, therefore, it may be ignored. This invention is not limited to the use of a single feed pipe 101. It may be preferable to use a plurality of feed pipes in order to minimise the constriction of flow inside biopsy (or material) channel 84. For example, four feed pipes may be used rather than the single feed pipe 101 shown in FIG. 2. It may be preferable to arrange the four feed pipes such that the total cross-section of the pipes equals the cross-section of the biopsy channel 84 in order to minimise a possible constriction that may occur. In this instance, the biopsy sample (or other material) would be gathered from four outlets (or inlets if material is to be delivered into the body) in the wall of outer conductor 85. The spacing between the feed pipes may be adjusted to minimise the mismatch caused by the introduction of the single feed pipe 101 into the system, i.e. this may remove the need for a separate impedance transformer (or matching stub) to be introduced into the tri-functional needle antenna design (already described above). More details on this aspect of the tri-functional needle antenna design are given at the end of this description, where results from initial electromagnetic field simulations for a typical needle antenna structure are given. The outer conductor 85 of the co-axial needle antenna structure 80 is the second conductor in the co-axial arrangement. Outer conductor 85 is connected to microwave connector 81 at the proximal end, and to ceramic tip and matching transformer 82 at the distal end. The outer conductor 85 is made from a suitable conductive material that provides rigidity for the overall needle antenna structure 80, and is preferably a biocompatible material to allow for percutaneous insertion into the human body. In theory, the thickness of outer conductor 85 only needs to be around six skin depths, which may be as low as 12 μm at the preferred frequency of operation. In practice, this will be increased by about a factor of ten in order to provide the required rigidity for the overall needle antenna structure 80 to enable it to be pushed through tissue layers unaided. From equation 4 and the drawing of the needle antenna 80 shown in FIG. 2, it can be seen that the need for limited conductor thickness has the advantage of maximising the diameter of tissue channel 84 and minimising the outer diameter of the overall needle antenna 80. A first dielectric 87 between inner conductor 88 and outer conductor 85 is used to determine the characteristic impedance of the co-axial section of needle antenna 80. First dielectric material 87 can also be used to increase the potential breakdown voltage between the two conductors and to ensure that the inner conductor is centrally aligned. It is preferable for first dielectric material 87 to exhibit a low dielectric loss at the frequency of operation. Possible materials for first dielectric material 87 include: low density polytetrafluorethylene (PTFE), expanded PTFE, or tape wrapped PTFE. In certain cases where the needle antenna structure is short, for example less than 10 cm, and where breakdown voltage is not an issue, and dielectric loading (where relative permittivity is greater than unity) is not required to reduce the overall diameter of the structure, it may be preferable to suspend the centre conductor in air. A second dielectric material 82 is used at the distal end of the needle antenna structure 80. It is preferable for the second dielectric material 82 to be a microwave ceramic material. The ceramic used is preferably a hard material that allows the needle antenna to be inserted into the body percutaneously, and exhibits a low loss at the frequency of operation to prevent the ceramic tip from reaching excessively high temperatures that may cause unwanted tissue damage. The tissue channel 84 is extended into second dielectric 82 to enable the extraction of tissue 290 to take place at the tip of the needle antenna structure 80. A hole with a diameter similar to that of the hole through centre conductor 88 may be made in dielectric material 82 to implement this feature. It may be desirable to perform an electromagnetic (EM) field simulation in order to optimise the effect of including the hole inside the ceramic cone. This feature provides the advantage of allowing the tissue sample, or biopsy, to take place at the same location as where the dielectric measurement is being performed to determine the tissue type or state. It may be preferable for the hole to be located in the side of second dielectric material 82 for the purpose of preventing tissue clogging up the cone tip and also to ensure that the cone tip is sharp enough to puncture through skin to allow for percutaneous needle insertion. It must be ensured that there is a good seal at the interface between the hollow centre conductor 88 and the hollow region of second dielectric 82 to ensure that there are no leakages in the system. This feature is important where the tissue transport channel 84 has a small diameter, especially where the size of a leakage point is comparable with the diameter of the transport channel 84. An additional function of second dielectric material 82 is that of performing an impedance match between the co-axial section of needle antenna 80 (described by equation 4) and a typical representative value for the complex impedance of treatment tissue 290. The impedance transformer may be a quarter-wave transformer, where the dielectric constant of the material used for 82 is chosen to create a matched condition between the dielectric constant of first dielectric material 87 and a representative dielectric constant for biological tissue 290. The interface between first and second dielectric materials 87 and 82 respectively should be well defined, i.e. if second dielectric material 82 is a hard ceramic and first dielectric material 87 is a low density PTFE, the hard ceramic should not squash or deform the low density PTFE, otherwise the characteristic impedance of the co-axial section in this region may be altered or the interface will be ill defined and this could lead to mismatches or reflections at this interface between first and second dielectric materials 87 and 82 respectively. A second matching transformer 83 is shown in needle antenna assembly 80. This may be a small metal stub or swage, which is used to cancel out an undesirable reactance (inductive or capacitive) seen at this point. It should be noted that the combined effect of matching provided by second dielectric material 82 and metal swage 83 is effective for providing impedance matching in the particular needle antenna structure 80 shown in FIG. 2, which has been optimised to deliver energy into a tumour using a particular tumour model. Each individual structure may require a particular solution to suit the particular geometry associated with the individual needle antenna 80, the frequency of operation and the representative tissue load 290. It may be desirable to perform an electromagnetic (EM) field simulation in order to optimise the particular antenna structure 80. An example EM field simulation package that has been used to optimise the antenna structures presented here is Computer Simulation Technology (CST) Microwave Studio.

The distal tip of needle antenna 80 should be sharp enough to allow for the antenna structure to be pushed through the skin without having to make an incision using a scalpel. Should it be necessary to make an incision, then this incision should be as small as possible, for example, less than 2 mm, and the incision should only be used to pierce the outer layer of the skin tissue. Once a small incision has been made, it should be possible for the antenna structure to be pushed through healthy tissue, towards the area of concern 120, with ease. It is advantageous to coat the needle antenna structure with a biocompatible material that provides a minimal amount of friction, for example, Parylene C.

It should be noted that pump 250 and vessel 260 may be replaced by a syringe (not shown). In this arrangement, tube 100 is used to connect needle antenna 80 to the syringe. The syringe may be a standard medical syringe, such as those used to remove blood samples from the human body or those used to inject drugs into the body. It may be preferable to use a syringe to extract fluid or cells rather than to use the pump and vessel arrangement described above.

Figure 3:
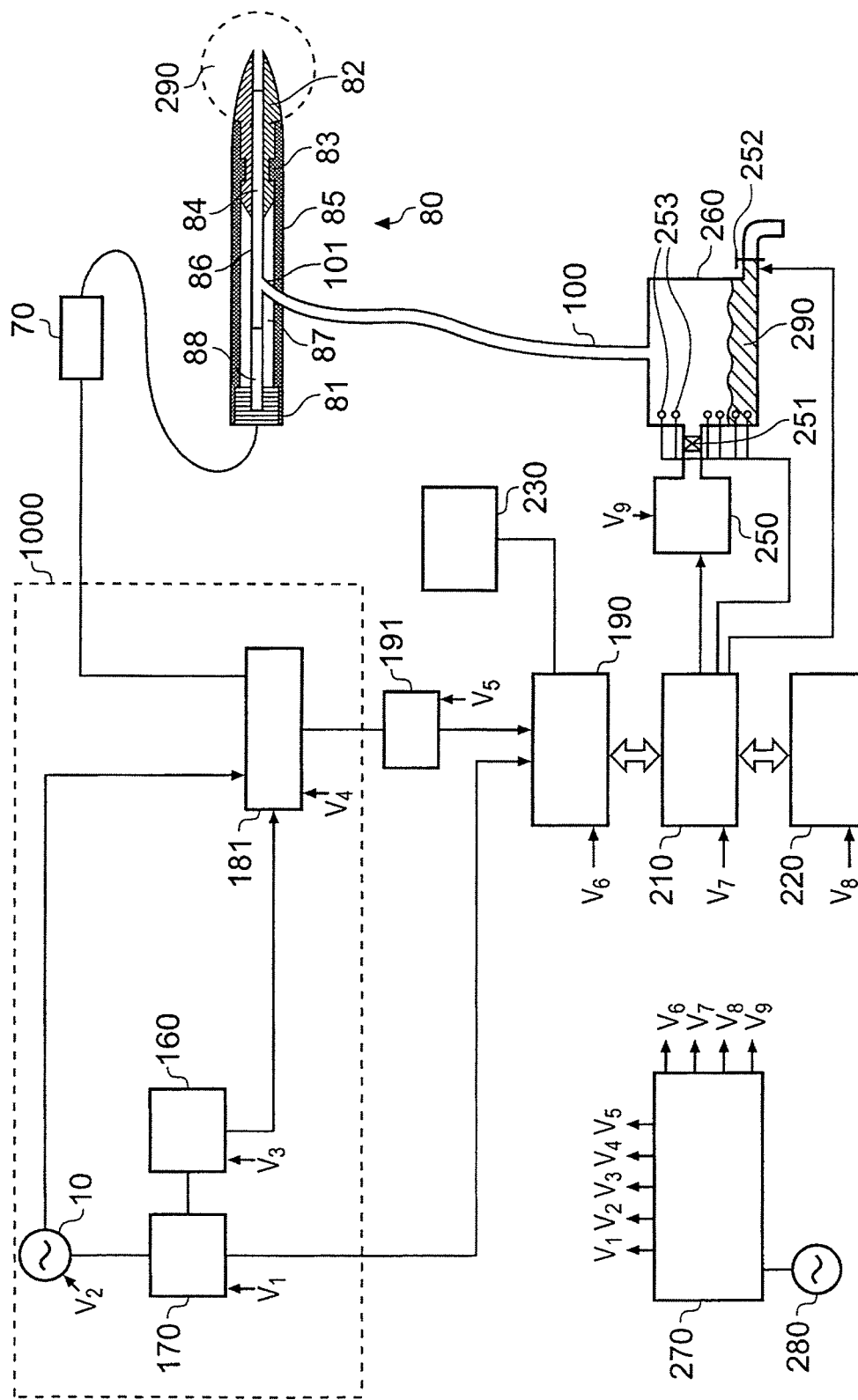
FIG. 3 is a diagram showing a needle biopsy apparatus that is a second embodiment of the invention.

FIG. 3 shows a diagram for a system that can be used solely to perform a tissue type/state measurement and take a needle biopsy. The functionality of the individual components and blocks has already been given. The only difference is that an analogue to digital converter (ADC) 191 is shown. The function of the ADC is to take the analogue signal from the receiver section of transceiver 181 and convert the analogue signal into a digital signal that is in an acceptable format for digital signal processor 190 to accept. Since the arrangement shown in FIG. 3 does not ablate tissue, the following units necessary for tri-functional operation are no longer required: power modulation and control unit 21, power amplifier 22, first forward and reflected power monitors 30, three-stub tuner 40, second forward and reflected power monitors 50, measurement/ablation switch 60, tuning stubs 130-132, linear actuators 141, and actuator controller 142. There are a number of advantages associated with using this system to percutaneously guide the needle antenna along the needle channel 121 to the cancerous tissue site 120 where tissue biopsy 290 is to be taken. It may be possible to locate the cancerous tissue with greater accuracy than that possible using conventional ultrasound or X-ray techniques. It may be desirable to use this system together with ultrasound or X-ray imaging to provide additional information regarding the accurate location of the cancerous tissue 120. It may be preferable to use this system in regions of the body where it is difficult to image tissue, i.e. where bones obstruct the image, or where the area of concern 120 is very small. This system may also be used to eliminate the need to take multiple tissue samples as is currently often the case. The region depicted by a dotted line 1000 shows the blocks needed for the operation of a sensitive low power transmitter and receiver (transceiver) unit 181; these blocks are broken down into individual microwave components in FIG. 4.

It should be possible for the given arrangement for the tissue type/state measurement and needle biopsy system (or unit) to be manufactured to produce a relatively small and portable location/biopsy unit due to the fact that this system does not require a high power tissue ablation amplifier and associated high current power supply, a forward/reflected power monitors and stub tuner, a stub actuator system, and an actuator controller unit.

Figure 4:
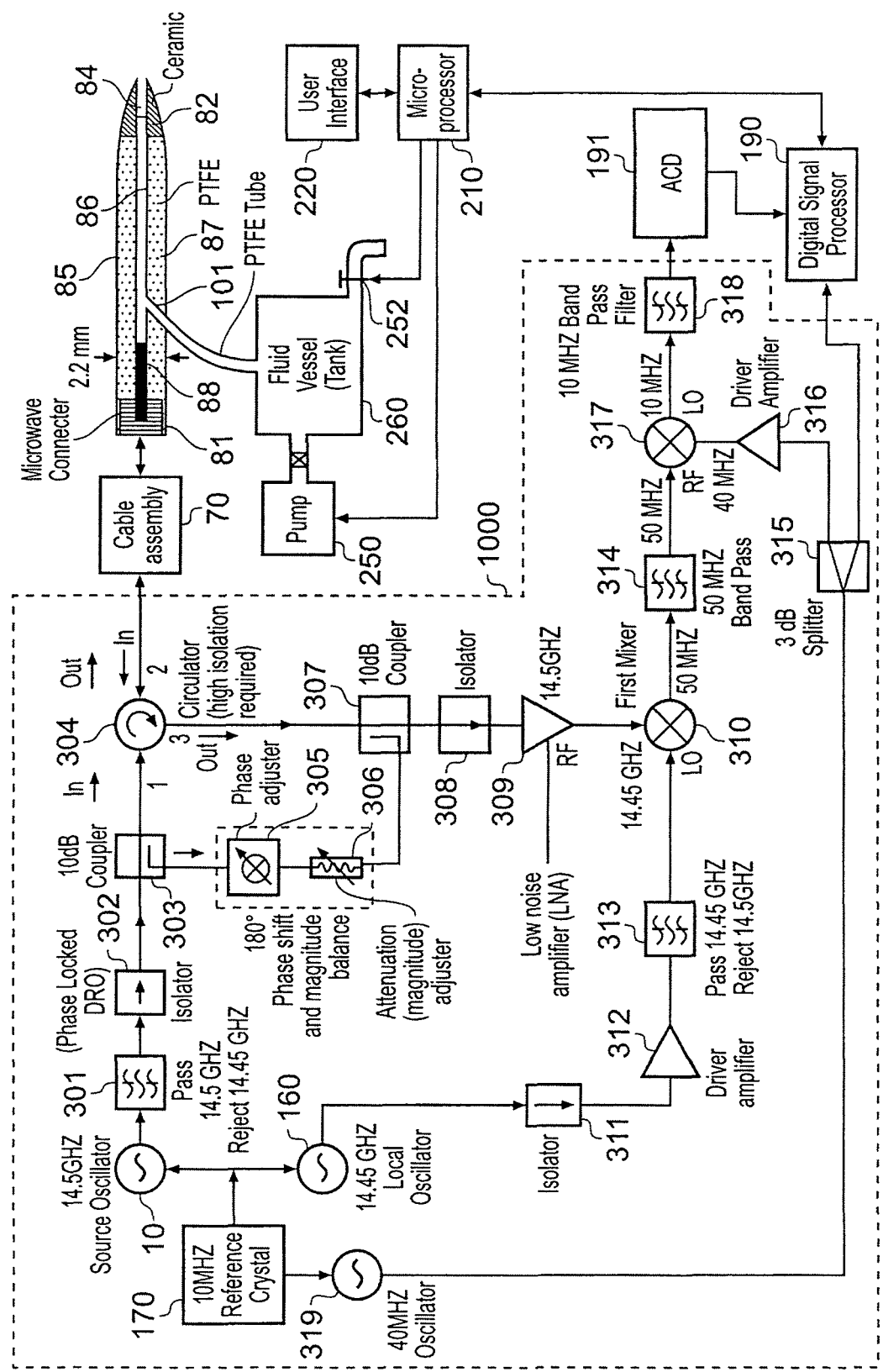
FIG. 4 illustrates the circuit layout for the transceiver shown in FIG. 3.

FIG. 4 shows a second diagram for the system that can be used solely to perform a tissue type/state measurement and take a needle biopsy. In this arrangement a specific embodiment for the low power transceiver circuit and signal oscillators 1000 is given. Except for individual microwave components contained within 1000, all components given in FIG. 4 are identical to those Previously discussed in this text above. The transceiver given here uses a microwave circulator 304 to separate the transmitting and receiving signal paths. The principle of operation of the transceiver is as follows: a low amplitude stable 14.5 GHz microwave signal, generated using source oscillator 10, passes through circulator 304 from port 1 to port 2 and is transmitted along cable assembly 70 through needle antenna 80 into the area of concern 120. A portion of the signal incident at the tissue/needle tip is then reflected back along the shaft of needle antenna 80, and cable assembly 70, back to port 2 of circulator 304. The internal path for the signal flowing back into circulator 304 is from port 2 to port 3. The received signal, passing from port 2 to port 3 of circulator 304, is then frequency down converted to provide an analogue signal at a frequency that is suitable for ADC 191 which is preferably a standard ADC. The transmitter circuit comprises source oscillator 10, which produces a single frequency at 14.5 GHz. The source 10 preferably comprises a dielectric resonator oscillator (DRO) that is phase locked to a temperature compensated crystal reference 170 to provide a single frequency with a small variation around the desired centre frequency, for example, a carrier frequency of 14.5 GHz with a variation of +/−1 KHz. The output from source oscillator 10 is connected to the input port of first band-pass filter 301, whose function is to pass the signal produced by source oscillator signal 10, but reject all other signals that are present at other frequencies. It is necessary for first band-pass filter 301 to block any signals present at the frequency of the first local oscillator 160. It is preferable for any signals that may be present at the frequency of local oscillator 160 to be attenuated by greater than 40 dB with respect to the signal level produced by source oscillator 10 in order to avoid the signal from first local oscillator 160 degrading the performance of the overall measurement system. The output from first band-pass filter 301 is connected to the input of first isolator 302, whose function is to ensure that any reflected signal present at port 1 of microwave circulator 304 cannot get back into the output of source oscillator 10 and affect the operation, for example, cause frequency variations due to load pulling or output power level variation. It is preferable that the signal isolation provided by isolator 302 is at least 20 dB. The output from isolator 302 is connected to the input of first directional coupler 303, whose function is to tap off a portion of the signal from source oscillator 10 in order to perform carrier cancellation for the received signal (this aspect is described later when we address the function of the receiver circuit). The output from the through path (main signal line) of first coupler 303 (the output port) is passed into port one of microwave circulator 304. Microwave circulator 304 acts as a roundabout for microwave signals, i.e. it allows signals to flow in one direction only; the signal paths through microwave circulator 304 are as follows: input on port 1 and output on port 2, input on port 2 and output on port 3, and input on port 3 and output on port 1. Ideally, it should not be possible for any signal to travel from port 1 to port 3, from port 3 to port 2, or from 2 to port 1. Also, path loss or insertion loss from ports 1 to 2, 2 to 3 and 3 to 1 should ideally be zero. In practice, some signal passes from port 1 to port 3, from port 3 to port 2, and from 2 to port 1, and the level of signal is determined by a property known as the isolation. For a good circulator, the value of isolation between the ports is as high as possible, for example, an optimised circulator may exhibit isolation of up to 35 dB if narrow bandwidth operation is required. Insertion loss between transmission ports is normally around 0.1 dB for a good circulator that can be operated in the frequency band that is of interest for this work. The output signal from the transmitter stage comes out of circulator 304 at port 2. This signal is then passed down cable assembly 70, through needle antenna 80 and into the area of concern 120. The level of signal emerging from the distal tip of needle antenna 80 is such that the biological tissue structure 290 will not be affected in any way, i.e. the power level will be less than 10 mW (10 dBm) and most likely will be around 1 mW (0 dBm).

On the receiver side, the signal reflected back along needle antenna 80, through cable assembly 70 arrives at port 2 of microwave circulator 304, where it travels from port 2 to port 3. The received signal coming out of port 3 goes into the input port of second directional coupler 307. First and second directional couplers 303 and 307 respectively form a part of a carrier cancellation circuit, which is used to increase the level of signal isolation between the transmitted and received signals. The carrier cancellation circuit comprises first directional coupler 303, a variable phase adjuster 305, a variable attenuator 306, and second directional coupler 307. The operation of the carrier cancellation circuit is as follows: a portion of the forward going signal from source 10, in this case −10 dB (or 10%), from the coupled port of first directional coupler 303 is fed into the input of phase adjuster 305, and the output from phase adjuster 305 is fed into the input of variable attenuator 306. The output from variable attenuator 306 is connected to the coupled port of second directional coupler 307. Second directional coupler 307 is configured such that the received signal from port 3 of microwave circulator 304 passes through the coupler in the 'low loss' path. As already mentioned, the purpose of the carrier cancellation circuit is to increase the isolation between the transmitted and received signals, i.e. reduce the effect of transmitted power at port 1 of circulator 304 getting through to port 3 of circulator 304 via the isolated path from port 1 to port 3. In addition, there will be signals that result from unwanted reflections due to mismatches in the output circuit between port 2 of circulator 304 and the needle antenna. The carrier cancellation circuit will also reduce the magnitude of these signals. In the configuration shown, the portion of the forward power from source oscillator 10 is adjusted in phase, using phase adjuster 305, and adjusted in magnitude, using attenuation adjuster 306, until the signal injected onto the main line of second directional coupler 307, via the coupled port of second directional coupler 307, is in anti-phase and equal in magnitude to the component of the unwanted transmitted signal coupling into port 3 of circulator 304 from port 1. If the signal that is coupled into the main line of second directional coupler 307 is in anti-phase and of the same magnitude as the unwanted signals that are added to the wanted received signal, the unwanted signals, which will be made up of both the finite isolation across ports 1 and 3 of circulator 304 and the unwanted reflections in the output path, will be removed and the signal seen at the output of second directional coupler 307 will be the wanted received signal. It is preferable for the coupling factors of first and second directional couplers 303 and 307 respectively to be the same; in this case 10 dB. It should be noted that the use of a single frequency transmitter signal is advantageous in terms of being able to increase the breakthrough isolation between ports 1 and 3 of circulator 304 due to the need for one fixed phase adjustment only; this feature also helps to enable effective cancellation of any reflected signals coming back along the reflected path due to mismatches that may be present along the path. This feature may also be used to increase the measurement sensitivity of the overall system.

The output port of second directional coupler 307 is connected to the input of second isolator 308, whose function is to prevent any mismatch or reflection at the input to low noise amplifier 309 from effecting the operation of the carrier cancellation circuit. The output from second isolator 308 is connected to the input port of the low noise amplifier 309, whose function is to boost the level of the received signal to a level that is acceptable at the RF input to first frequency mixer 310 to enable the frequency mixer 310 to operate. It is preferable for a amplifier 309 to be a low noise amplifier to ensure that the received signal at its input is not corrupted with noise, for example, thermal or shot noise produced by the amplifier itself, which will add to the received signal and limit the sensitivity of the measurement system. The local oscillator input signal to first frequency mixer is a 14.45 GHz signal that is produced by first local oscillator source 160. The first local oscillator source 160 is preferably a dielectric resonator oscillator (DRO), which is phase locked to a temperature compensated crystal reference 170 to provide a single frequency with a small variation around the desired centre frequency, for example, a 14.45 GHz signal with a variation of less than +/−1 kHz. It is preferable for the source oscillator 10 (and measured RF signal) to be synchronised to first local oscillator 160, and this may be achieved by using the same crystal reference 170. The output from first local oscillator 160 is connected to the input of third signal isolator 311, whose purpose is to prevent any mismatch or reflected signal seen at the input to first driver amplifier 312 from varying the frequency produced by first local oscillator 160 caused by load pulling. The output of third isolator 311 is connected to the input of the first driver amplifier 312, whose function is to boost the level of the signal produced by first local oscillator 160 to a level that is acceptable by first frequency mixer 310 as a local oscillator signal that will enable the first mixer 310 to operate correctly. The output from driver amplifier 312 is connected to the input of second band-pass filter 313, whose function is to pass the signal produced by first local oscillator signal 160, but reject all other signals that are present at other frequencies. It is necessary for second band-pass filter 313 to block any signals present at the frequency of the source oscillator 10. It is preferable for any signals that may be present at the frequency of the source oscillator 10 to be attenuated by greater than 40 dB with respect to the signal level produced by first local oscillator 160 in order to avoid the signal from source oscillator 10 degrading the performance of the overall measurement system. The output from second band-pass filter 313 is fed into the local oscillator input to first frequency mixer 310. First frequency mixer 310 produces two output frequencies, which are the sum and difference of the RF and local oscillator (LO) frequencies, i.e. RF+LO and RF−LO. In this particular embodiment, 14.5 GHz+14.45 GHz=28.95 GHz, and 14.5 GHz−14.45 GHz=50 MHz. These frequencies are known as intermediate frequencies (IF). The 50 MHz IF is required in this work as this is a practical frequency that can be used to extract magnitude and phase from the measurement signal. The output IF from first frequency mixer 310 is fed into the input of a third band-pass filter 314, whose function is to filter out the signal at the sum frequency (RF+LO) and any other undesirable signals that may be present, for example, the source oscillator 10 signal, the first local oscillator 160 signal, the crystal reference signal 170, and the second local oscillator signal. The band-pass filter shown in the particular embodiment given in FIG. 4 allows the 50 MHz IF signal to pass through the filter unadulterated. The output from third band-pass filter 314 is fed into the RF input to second frequency mixer 317, whose function is to further frequency down-convert the 50 MHz IF signal. The local oscillator input to second frequency mixer 317 comes from second local oscillator source 319, which is preferably a crystal oscillator or a voltage controlled oscillator (VCO) module. It is preferable for second local oscillator source 319 to be connected to temperature compensated crystal reference 170 to provide a single frequency with a small variation around the desired centre frequency. It is required that the main source oscillator 10, the first local oscillator 160, and the second local oscillator 319 be synchronised together, and this may be achieved using the same crystal reference 170. The output from second local oscillator 319 is connected to the input of a two way power splitter 315, whose function is to split the power level produced by second local oscillator 319 into two equal parts without causing an impedance mismatch. It may be preferable to use a co-axial 3 dB power splitter. The first output from power splitter 315 is fed into second driver amplifier 316, whose function is to boost the level of the signal produced by second local oscillator 319 to a level that is acceptable by second frequency mixer 317 as a local oscillator signal that will enable the second frequency mixer 317 to operate correctly. The output from second driver amplifier 316 is fed into the local oscillator input of second frequency mixer 317. Second frequency mixer 317 produces two output frequencies, which are the sum and difference of the RF and local oscillator (LO) frequencies, i.e. RF+LO and RF−LO. In this particular embodiment, 50 MHz+40 MHz=90 MHz, and 50 MHz−40 MHz=10 MHz. The 10 MHz IF is required in this work as this is a practical frequency that can be used by a standard ADC 191 to extract magnitude and phase from the measurement signal. The advantage of using a lower frequency ADC is that greater linearity and dynamic range is normally available. The output IF from second frequency mixer 317 is fed into the input of a fourth band-pass filter 318, whose function is to filter out the signal at sum frequency (RF+LO), in this case 90 MHz, and any other undesirable signals that may be present, for example, the source oscillator 10 signal, the first local oscillator 160 signal, the crystal reference signal 170, and/or the second local oscillator signal. The band-pass filter shown in the particular embodiment given in FIG. 4 allows the 10 MHz IF signal to pass through the filter unadulterated. The second output from power splitter 315 is fed into the digital signal processor 190 and is used for timing functions and synchronisation of the measurement signals. All other blocks and components contained within FIG. 4 have already been described in detail above.

Figure 5:
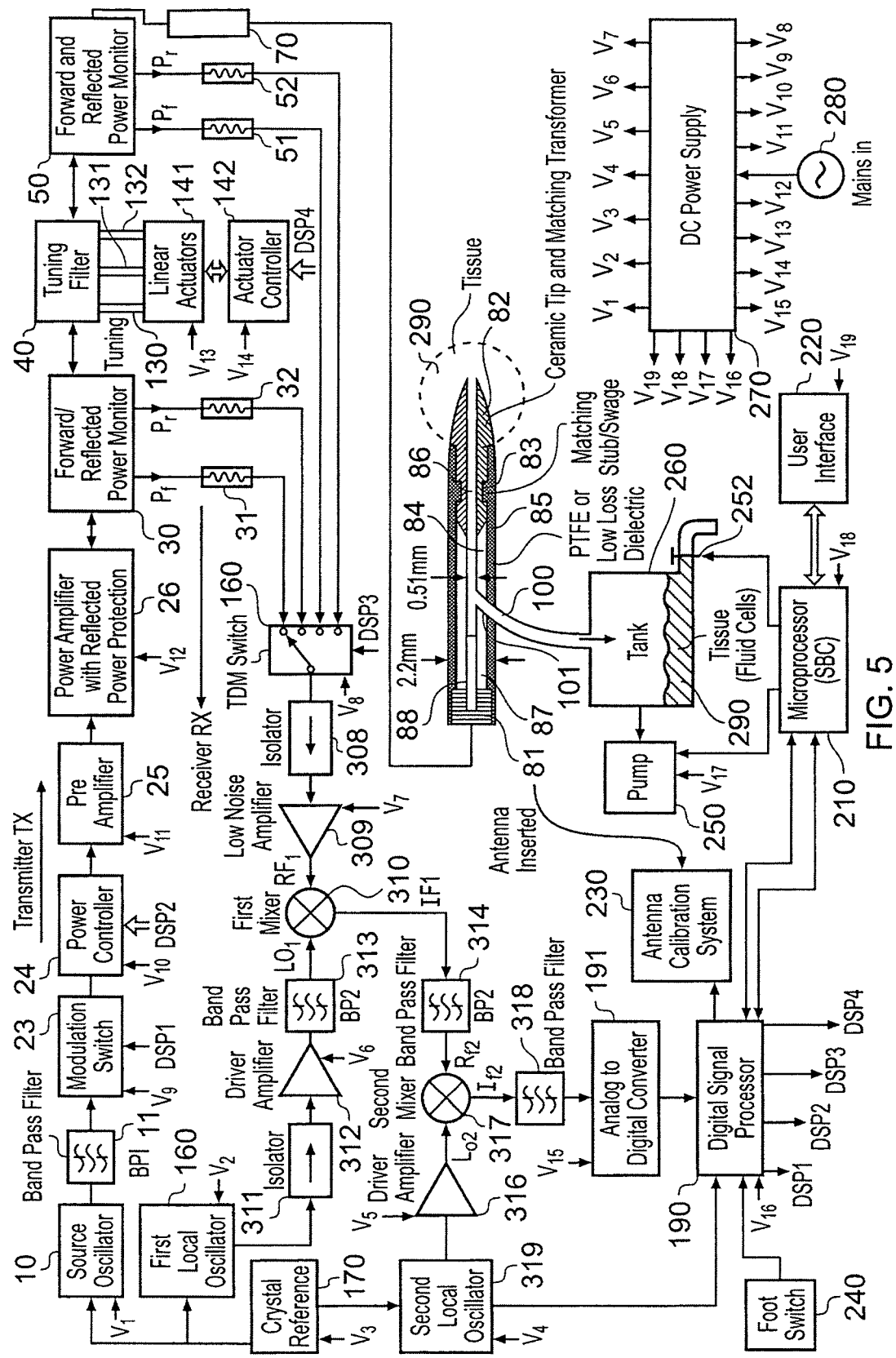
FIG. 5 is a diagram showing a needle biopsy apparatus that is a third embodiment of the invention.

FIG. 5 shows a system for producing controlled ablation of the channel or track made by the needle antenna and/or to produce controlled ablation of the tissue or tumour to be treated, and for taking a tissue biopsy. The receiver shown in FIG. 5 is identical to that shown in FIG. 4, and described above, from the input port of signal isolator 309, i.e. the operation and configuration of components: 308, 309, 310, 160, 170, 311, 312, 313, 314, 319, 316, 317, 318 and 191 are the same as that given in FIG. 4, and described above. Due to the fact that the function of the arrangement shown in FIG. 5 is to enable controlled ablation of the needle channel, or track, and/or to enable controlled ablation of the treatment tissue, the receiver uses signals taken from forward and reflected power directional couplers connected either side of tuning filter 40, to control the position of tuning rods 130, 131, and 132, which enable the impedance seen at the tip of needle antenna 80 to be matched with the output impedance of power amplifier 26 to provide efficient power delivery into tissue. The operation of the system to enable desired constant power to be delivered into the changing tissue load impedance based on a user controlled demand requires low insertion loss between the tuning filter 40 and the distal tip of needle antenna 80. The combination of tuning filter 40, forward and reflected power monitor 50, cable assembly 70, and needle antenna 80 may be considered as a single resonant filter. The filter should have as high a quality factor (Q) as possible since the filter operates as a resonant cavity, where multiple reflections between the tuning filter 40 and the distal tip of needle antenna 80 are used to enable effective impedance matching between the power amplifier 26 and tissue load 290. In the arrangement shown in FIG. 5, the output from source oscillator 10 (already described) is fed into the input of first band-pass filter 11, whose function is to pass the signal produced by source oscillator signal 10, but reject all other signals that are present at other frequencies. It is necessary for first band-pass filter 11 to block any signals present at the frequency of the first local oscillator 160. It is preferable for any signals that may be present at the frequency of local oscillator 160 to be attenuated by greater than 40 dB with respect to the signal level produced by source oscillator 10 in order to avoid the signal from first local oscillator 160 degrading the performance of the impedance matching system. The output from first band-pass filter 11 is fed into modulation switch 23, whose function is to switch (or modulate) the signal produced by source oscillator 10 by toggling signal control line DSP1, which is controlled by digital signal processor 190. The output from modulation switch 23 is fed into the input of power controller 24, whose function is to attenuate the level of power produced by source oscillator 10 to provide a means of controlling the power level produced at the output of power amplifier 26, and subsequently control the level of power delivered into biological tissue 290. The level of attenuation is determined by the signals present on digital control lines DSP2, which are set by digital signal processor 190. The output signal from power controller 24 is fed into the input of pre-amplifier 25, whose function is to amplify the incident signal by a fixed amount of gain. It may be preferable to use high gain MMIC devices in pre-amplifier 25. The output from pre-amplifier 25 is fed into the input to power amplifier 26, whose function is to boost the power from the output of pre-amplifier 25 to a level that can be used to cause efficient tissue ablation. It is normal for power amplifier output stages, such as those associated with power amplifier 26, to use low gain, high power microwave transistors, and it may be necessary to combine the output from a number of such power transistors in order to produce the desired output power level from the system. The output from power amplifier 26 is protected against damage that may be caused by reflected signals returning to the output of amplifier 26 using a microwave circulator with a 50Ω power dump load connected to port 3, i.e. the port where reflected power will be incident after it has traveled back along cable assembly 70. This arrangement also protects the amplifier from load pulling caused by changes in the impedance seen at the output point of the power devices. Without protection, such load pulling may cause the amplifier to act as a power oscillator, which will inevitably result in damage occurring to the amplifier. The output from power amplifier 26 is connected to the input of first forward/reflected power monitor 30, whose function is to provide a portion of the forward and reflected power that can be fed into the microwave receiver for subsequent processing for use in controlling the position of the tuning stubs to create the necessary matched condition. The output from first forward/reflected power monitor 30 is fed into the input to tuning filter 40, whose function is to produce the matched condition and create a resonant cavity between the distal tip of needle antenna 80 and tuning filter 40. The three tuning stubs 130, 131, and 132 are controlled using suitable linear actuators 141. The linear actuators 141 are connected to actuator controller 142, whose control signals are provided by digital control lines DSP4, which are connected to digital signal processor 190. The output from tuning filter 40 is connected to the input second forward/reflected power monitor 50, whose function is to provide a portion of the forward and reflected power that can be fed into the microwave receiver for subsequent processing for use in controlling the position of the tuning stubs to create the necessary matched condition to enable precise control of energy being delivered into tissue structures. This feature enables uniform ablation of the track or channel subsequent to the needle biopsy. The coupled ports from first forward/reflected power monitor 30 and second forward/reflected power monitor 50 are fed into a single-pole-four-throw (SP4T) time domain multiplexing switch 150, whose function is to transfer measurement signals from first and second forward/reflected power directional couplers 30 and 50 respectively into the measurement receiver (comprising: 308, 309, 310, 160, 170, 311, 312, 313, 314, 319, 316, 317, 318 and 191) and digital signal processor 190 to enable phase and magnitude extraction and subsequent processing to determine the required position of tuning stubs 130, 131, 132 to set-up the resonant or matched condition. Fixed attenuators 31, 32, 51, 52 are shown connected between the coupled ports of forward/reflected power monitors 30, 50 and the four input ports connected to SP4T switch 150. The switch position is controlled using control signal DSP3, which is connected to digital signal processor 190. The signals from first and second forward/reflected power monitors 30 and 50 respectively are polled using SP4T switch 150 at a high enough speed to enable phase and magnitude information from the forward and reflected signals measured at the input and output ports of tuning filter 40, to be compared with one another to enable the necessary adjustment of the position of the tuning stubs (rods) to be determined.

Needle Structures

FIG. 6 illustrates the effect of skin depth on a solid conductor 500. It can be seen that the amount of cross-sectional area required for the microwave energy (or signal) to flow 520 is small compared with the total cross-sectional area of the conductor. The region of the conductor where no conductor is required 510 is effectively transparent to the microwave energy that is propagating (or flowing) backwards and forwards along conductor 500. The region of conductor 510 can be made hollow and may be filled with any material, for example, biological fluid, biological cells, drugs, radioactive dyes, radiological contrast media, saline, or water.

FIG. 7 shows a graph of the percentage power transferred as a function of the thickness of the metallisation layer, or, put in another way, the amount of cross-sectional area required for four commonly used conductive materials at an operating frequency of 14.5 GHz. The materials chosen are: copper, silver, nickel and steel. It can be seen that copper and silver are very similar, with silver allowing for a slightly thinner layer of metallisation to be deposited. It can be seen that for both copper and silver, the required thickness for all of the microwave energy to be transported is 8 μm. Nickel and steel require thicker layers of metallisation to be deposited to enable all of the microwave energy to flow along the conductor. Steel requires the thickest layer of metallisation to be deposited to provide a conduit for all of the microwave energy to flow. Calculations show that with steel as the conductor, 99.9% of the microwave energy is transferred when the thickness is 12.91 μm.

FIG. 8 shows a detailed drawing of a representative tri-functional needle antenna construction. The salient features of the structure have already been described above. In the construction shown in FIG. 8, the biopsy channel 84 takes tissue 290 through the side of a cone tip, made from second dielectric material 82. It is preferable for the second dielectric material 82 to be a hard material; a microwave ceramic maybe used as the material of choice. This construction, where the inlet to the biopsy channel 84 is located at the side of the ceramic cone tip, has the advantage of allowing the tip of the cone to be sharp to facilitate percutaneous insertion through biological tissue. In this drawing, the outer diameter of the overall structure of the needle antenna is denoted by the letter a 800, the thickness of the layer of metallisation of the outer conductor is denoted by the letter b 801, the inner diameter of the outer conductor is denoted by the letter c 802, the outer diameter of the inner conductor is denoted by the letter e 804, the inner diameter of the inner conductor is denoted by the letter d 803, and the thickness of the inner conductor is denoted by the letter f 805. Dimensions c 802 and e 804 are used in calculating the characteristic impedance of the co-axial structure; equation 4 can be used for the calculation.

Figure 9A:
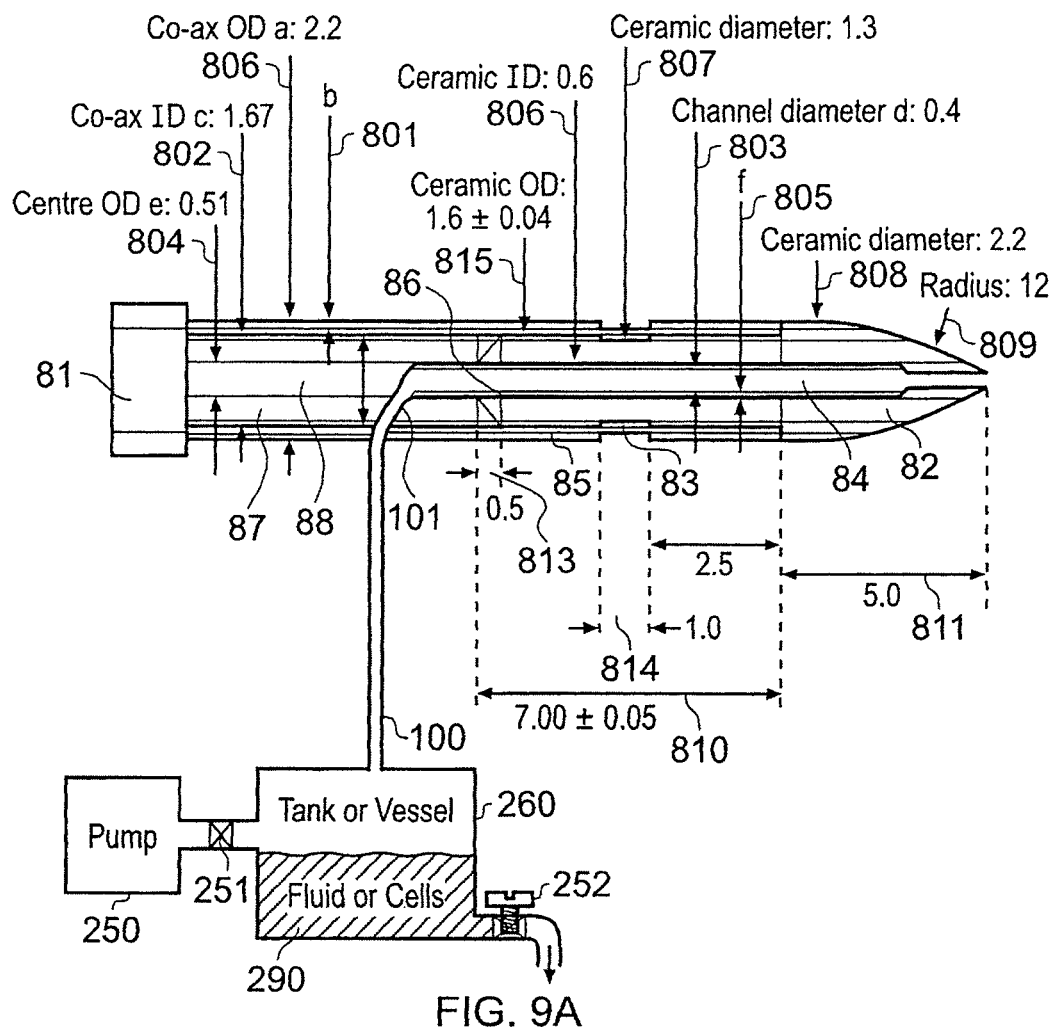
FIGS. 9a and 9b illustrate a needle antenna that is a sixth embodiment of the invention.
Figure 9B:
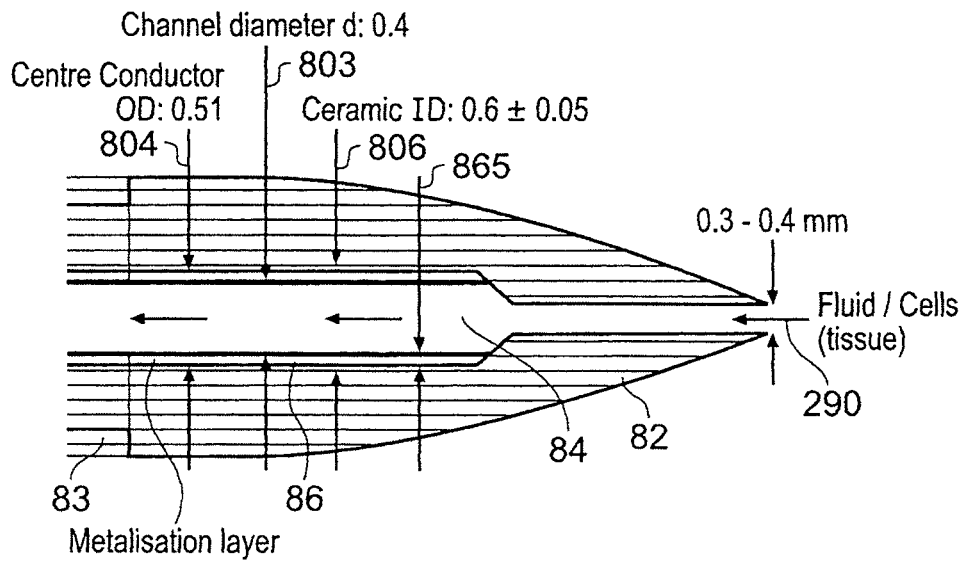

FIG. 9a gives a specific embodiment for a practical tri-functional needle antenna, where the inlet to the biopsy channel 84 is in the centre of the structure. The specific embodiment shown in FIG. 9a includes the following dimensions: the radius of the second dielectric 809, the outside diameter of the second dielectric 808, the diameter of the second dielectric when inserted inside the outer conductor of the co-axial structure 815, the diameter of the second dielectric 82 to enable the second matching transformer swage 83 to be fitted 807, the length of the taper at the proximal end of second dielectric material 813, the length of the metal swage 814, the inside diameter of the second dielectric 806, the length of the second dielectric between the end of the co-axial structure and the distal tip of the needle antenna 811, and the length of the second dielectric material inside the co-axial structure 810. The geometry of the second dielectric material 82 has been designed to act as a first impedance transformer to perform impedance matching between the complex impedance of a representative tissue (or tumour) structure 290, the second dielectric material 82, and the first dielectric material 87. Metal swage 83 is a second matching transformer and is used to perform an impedance match between the co-axial structure and second dielectric material 82. Second transformer 83 may be a single stub, with a capacitive or inductive reactance that may be used to cancel out reactive elements that may inherently exist in the region between first and second dielectric materials 87 and 82 respectively. FIG. 9b shows an expanded view of the tip of the needle antenna 80, where the biopsy channel 84 passes through the centre of the distal tip. In the instance where dynamic impedance matching is used, it is not necessary to design the structure to provide a good match into a specific impedance, since the operation of the tuner should enable the antenna to match into any impedance.

Figure 10A:
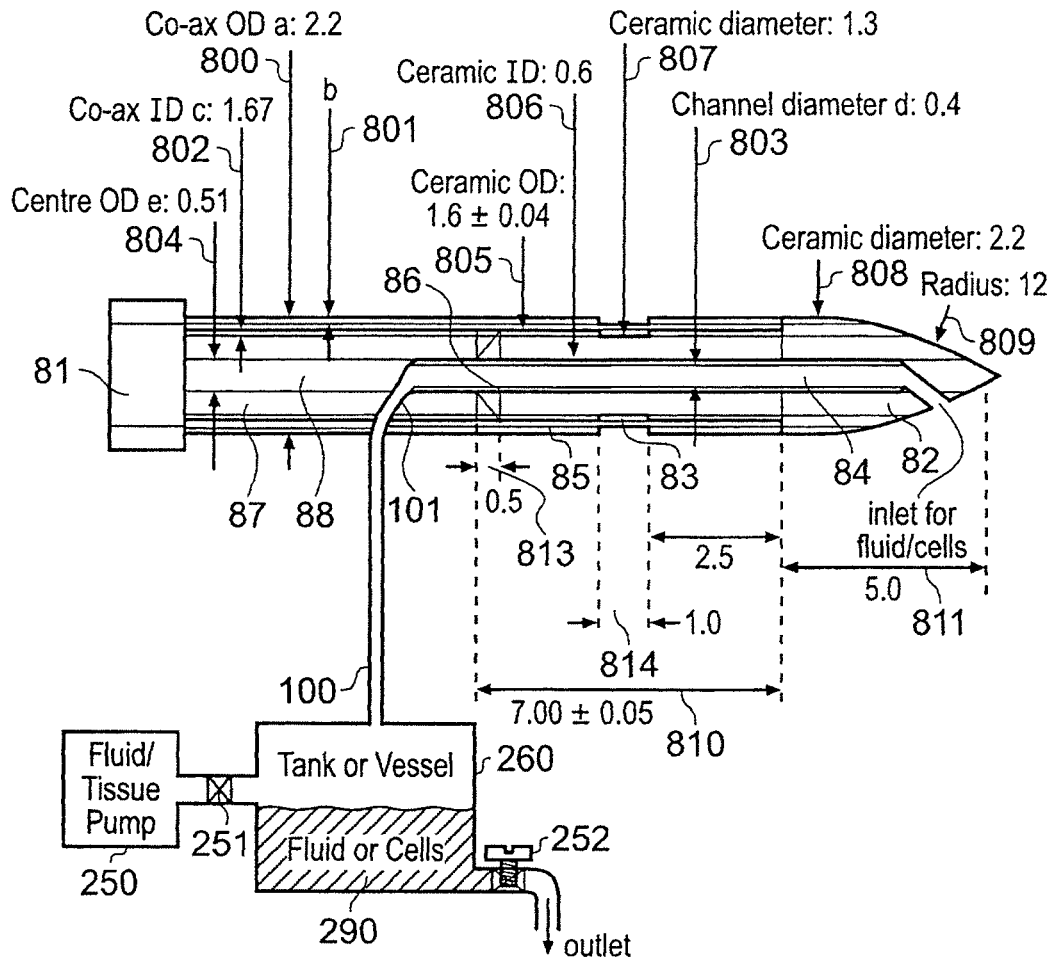
FIGS. 10a and 10b illustrate a needle antenna that is a seventh embodiment of the invention.
Figure 10B:
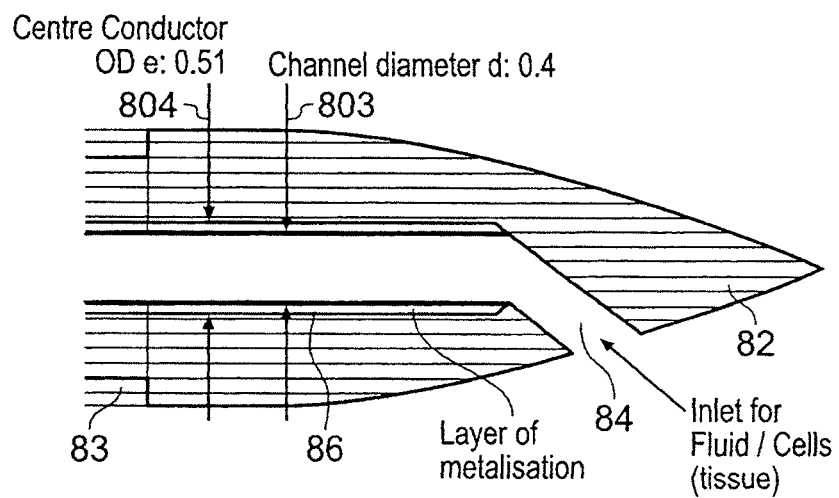

FIG. 10a gives a specific embodiment for a practical tri-functional needle antenna, where the inlet to the biopsy channel 84 takes tissue 290 through the side of the cone tip, made from second dielectric material 82. It is preferable for the second dielectric material 82 to be a hard material; a microwave ceramic maybe the material of choice. FIG. 10b shows an expanded view of the tip of the needle antenna 80, where the biopsy channel 84 passes through the side of the ceramic cone made from second dielectric material 82. All other details relating to FIGS. 10a and 10b have already been given in this description.

Electromagnetic Field Simulations

Electromagnetic field simulations have been performed to examine the effects of including the biopsy channel 84 within the needle antenna structure 80.

The initial simulation results show that a 0.4 mm diameter biopsy (or material) channel 84 can be incorporated down the centre of inner conductor 88 of the needle antenna 80. In the simulation model used here, the channel 84 has been extended out through the ceramic tip 82, so that biopsies may be taken through the biopsy (or material) channel 84. As far as microwave parameters are concerned, it has been shown that the hole or channel 84 in the centre conductor 88 has no effect. However, the hole in the ceramic tip 82 does affect the microwave parameters, as might be expected, but this may be compensated for using the dynamic impedance matching and tuning mechanism described earlier in this description as a part of the invention.

Simulation Results

The biopsy channel 84 was modelled running down the axis of the centre-conductor 88 of the coaxial line, and through the end of the ceramic tip 82. The channel 84 extended for 2 mm from the input port to the end of the ceramic tip 82, 25 mm from the input port. The entire biopsy channel 84 was modelled in every case as being full of the same material 290 as that surrounding the tri-functional needle antenna 80 i.e. it is assumed that the tip of the needle is immersed inside the cancerous lesion. The tissue materials 290 used were: tumour, breast fat and air.

Figure 11:
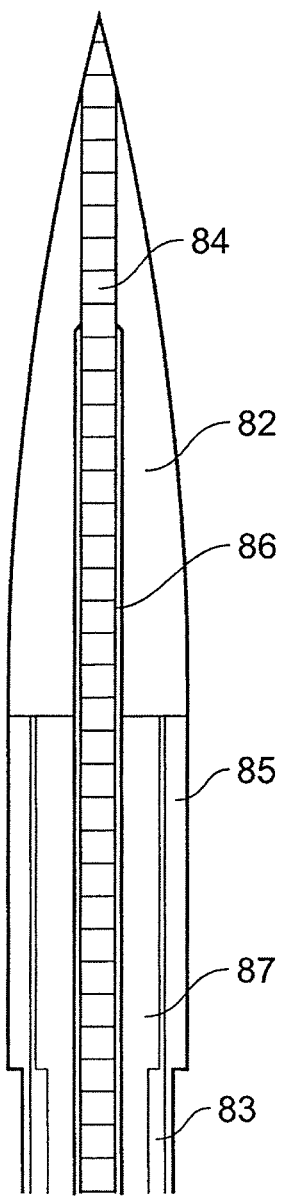
FIG. 11 is a cross-section through a model of a needle antenna according to the present invention for use in a computer simulation.

A cross-section of the tri-functional needle antenna 80 is shown in FIG. 11. The biopsy channel 84 is shown with horizontal hatching. In each case the presence of the biopsy sample 290 in the tip of the ceramic inlet 82 modified the match to the needle antenna 80. The presence of the biopsy sample 290 inside the channel 84 of the centre-conductor 88 has no effect on the microwave performance of the needle antenna 80, except for the first millimeter at the tip. This is because the wall 86 of the centre-conductor 88 is more than several skin-depths in thickness, so that the biopsy sample 290 is shielded from fields outside the centre-conductor 88, and the biopsy channel 84 is well below the cut-off frequency for propagation of waves along the channel 84, even when taking into account that the biopsy sample 290 may have a very high dielectric constant (or permittivity). For a dielectric constant of 50, which is the highest likely to be found in the use envisaged, the tube or channel 84 would need to be over 3.5 mm in internal diameter for propagation to take place, and even if this were to be the case, the high losses in the sample 290 would result in very rapid attenuation of the signal in the first few millimeters.

Figure 12:
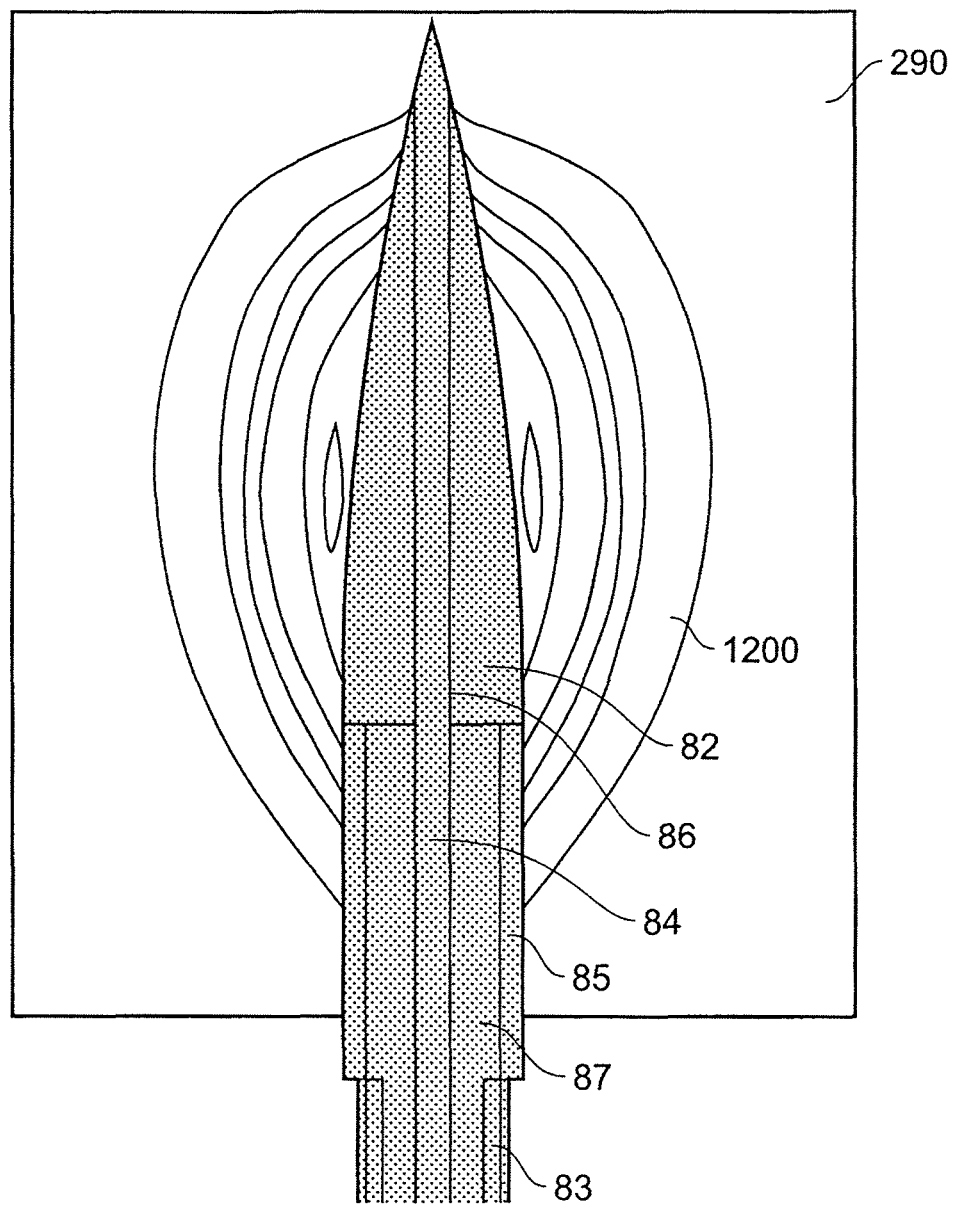
FIG. 12 shows the result of a simulation of the energy distribution from the needle antenna shown in FIG. 11.

FIG. 12 shows the energy distribution 1200 for the tri-functional needle antenna 80. Power density 1200 inside the biopsy channel 84, the ceramic tip 82, and the surrounding tumour 290 is shown. It can be seen that there is very little loss in the biopsy channel 84.

Figure 13:
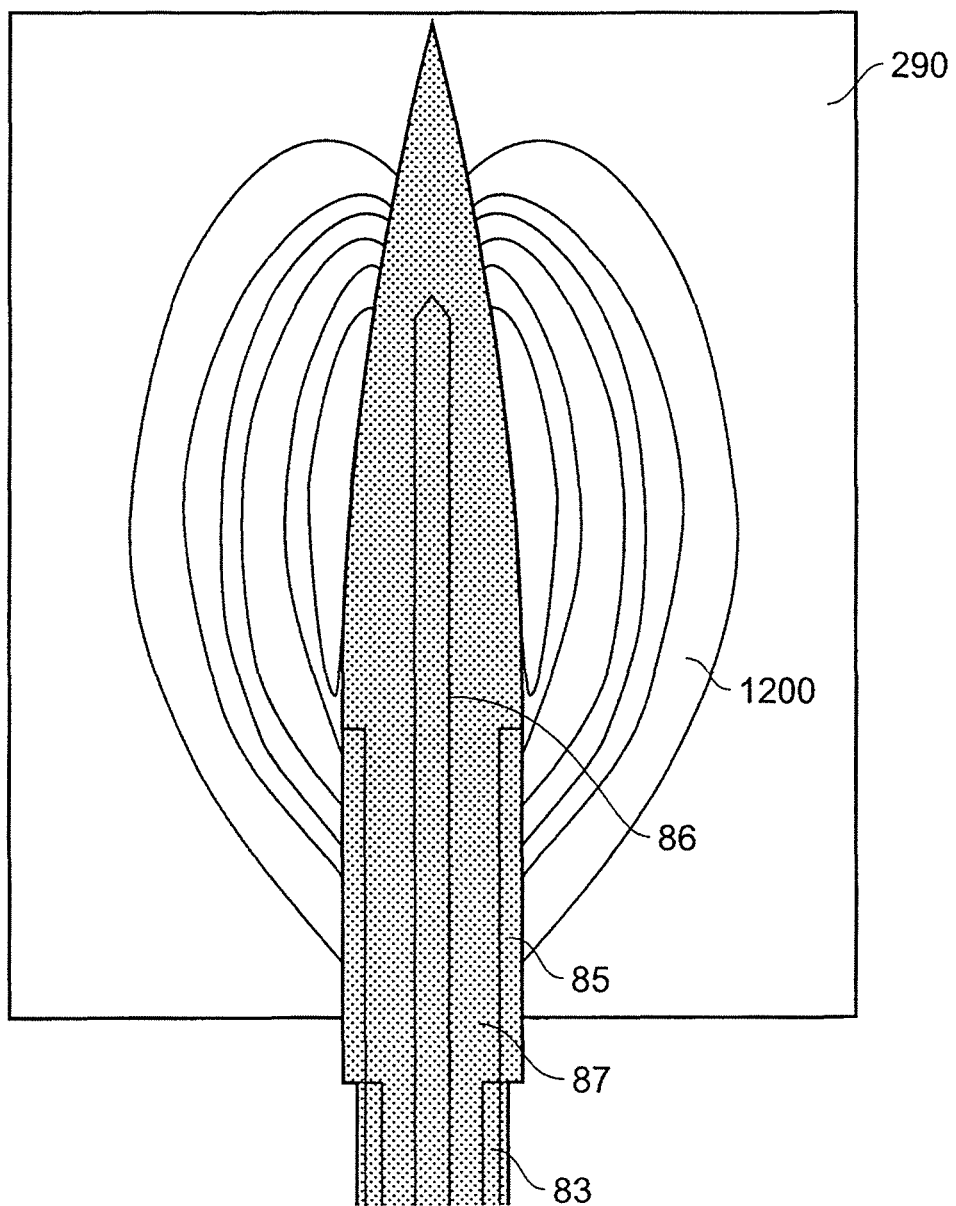
FIG. 13 shown the result of a simulation similar to FIG. 12 but where there is no biopsy channel through the centre of the needle.

FIG. 13 shows the energy distribution for the needle antenna 80 without the biopsy channel present. It can be seen that the presence of the biopsy channel 84 results in more power absorption near the tip of the needle antenna. There is also a slight lowering of the peak absorption. This is probably due to two effects: the first is that when a biopsy channel 84 is present, the power is spread over a larger volume, since there is more power absorbed near the tip, and secondly, the biopsy sample 290 worsens the match between the needle antenna 80 and the biological tissue 290, so slightly less power is delivered in total. As already mentioned, the dynamic tuning mechanism, using the three-stub tuner, will recover most of the loss due to the second effect. This mismatched condition could also be tuned out by a slight re-design of the needle antenna, and this approach would be preferable in the instance where the current invention is used only to take a tissue biopsy for measuring the dielectric properties of the layers of biological tissue. The change in the power absorption pattern or energy distribution near the tip when the biopsy channel 84 is introduced may be advantageous as the simulations indicate that the addition of the channel 84 results in more tissue heating near the tip of the structure 80. This may be particularly useful in track (or channel) sealing where it is required to minimise the amount of ablation of healthy tissue whilst preventing cancerous cells from being left behind.

Figure 14:
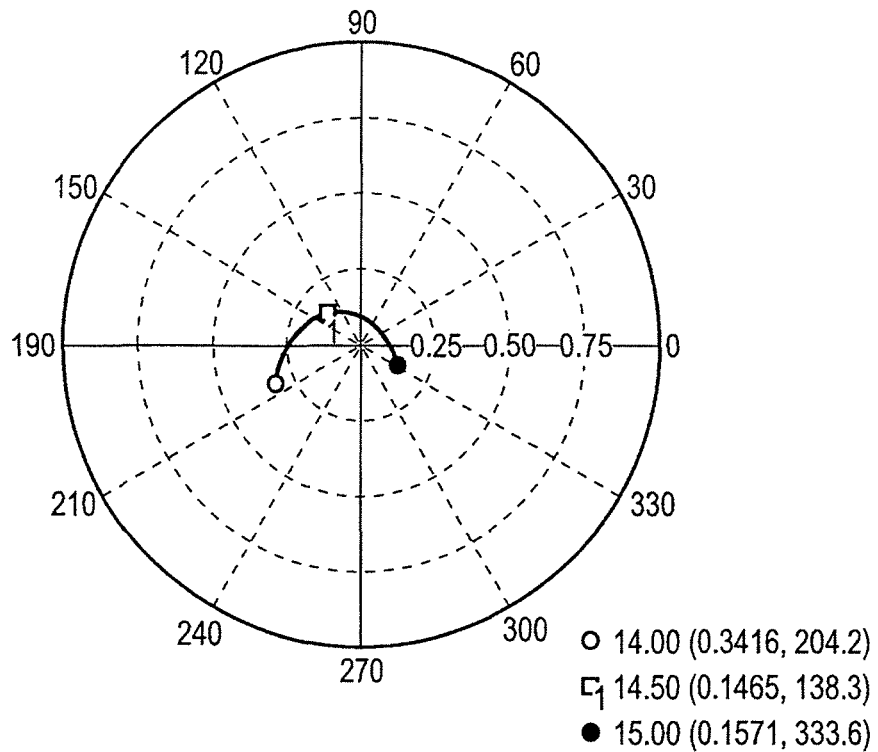
FIGS. 14 and 15 are diagrams illustrating the impedance match for a needle antenna with and without a biopsy channel.
Figure 15:
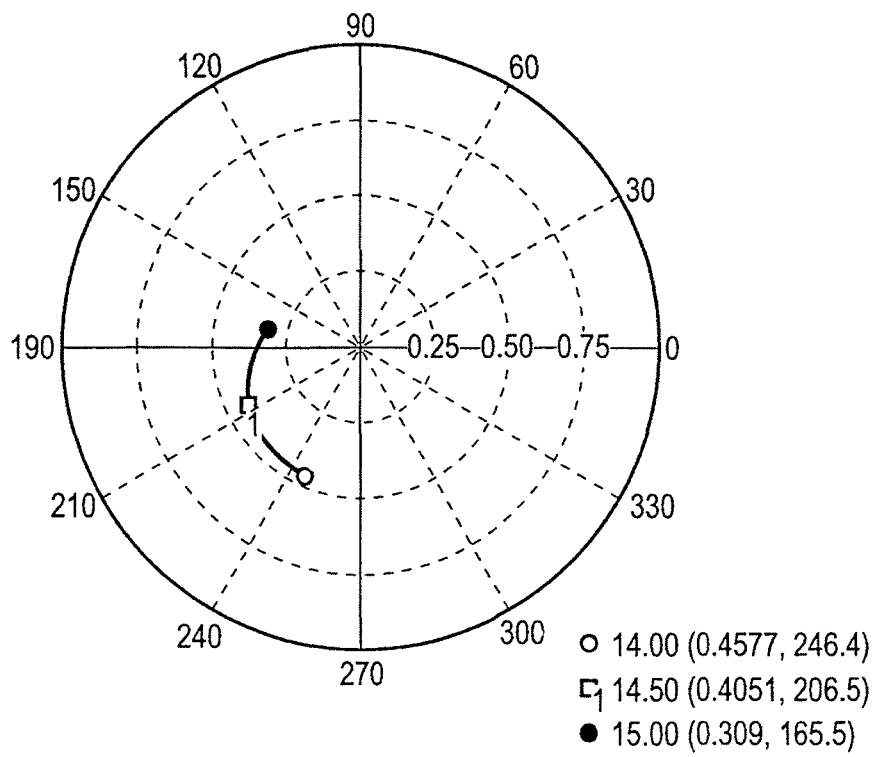

The change in impedance match introduced by the biopsy channel 84 at the tip of the needle antenna 80 is illustrated in FIGS. 14 and 15. FIG. 14 shows the impedance match for the needle antenna 80 with no biopsy channel present, and FIG. 15 shows the impedance match of the new tri-functional needle antenna 80, which includes the biopsy channel 84. The impedance match is shown for a range of frequencies of between 14 GHz and 15 GHz, with a square marker at 14.5 GHz.

Figure 16:
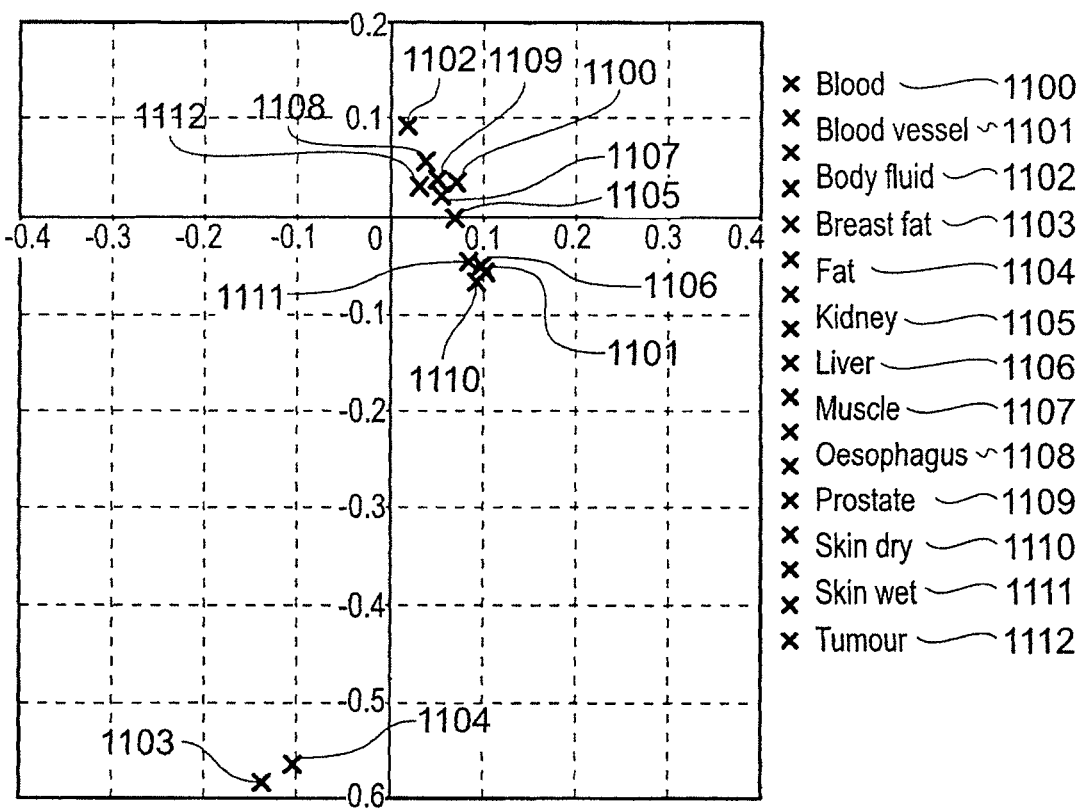
FIG. 16 is a plot showing the impedance values of various materials on a Smith chart.

It can be seen that there is a significant change in the impedance match between the two structures. The phase has been rotated by about 80 degrees, and the return loss has changed from about 17 dB to around 8 dB. Impedance values referenced to the proximal end of the needle antenna assembly 80, with the biopsy channel 84 included, for various representative biological tissue structures; i.e. structures that the distal tip of the needle antenna 80 may be subjected to in practice is shown in FIG. 16. These simulation results show a region near the centre of the polar plot, where the axes cross. The scale in FIG. 16 is approximately twice as large as in FIGS. 14 and 15. It can be seen from the simulation results given in FIG. 16 that it is possible to differentiate between various types of biological tissue even when the biopsy channel 84 is included in the overall needle antenna structure 80; this indicates that the current invention may be used to take a tissue biopsy and also effectively measure the various dielectric properties of the biological system.

It may be observed that the cluster of points towards the top of FIG. 16 is for blood-rich tissue, and the points at the bottom are for fatty tissue.

In order to remove the biopsy sample 290 from the distal tip of the tri-functional needle antenna 80, a connection pipe 101 is required between the wall of the inner conductor 88 and the wall of the outer conductor 85 to a feed pipe 100. At some point, the connection pipe 101 must pass through the wall of the coaxial feed. A number of designs of connection pipes 101 have been modelled in this work. In the end, four connection pipes 101, 102, 103, 104 were used with a total cross section equal to the cross-section of the biopsy tube 84 through the distal tip of the needle antenna. The total cross-section is a compromise between minimising the constriction of flow of the biopsy sample 290, and leaving sufficient width of wall 86 on the inner conductor 88, between connection pipes 101, 102,104,104, to provide good microwave conduction, and physical strength.

A ring of connection pipes 101,102,103,104 near to the proximal feed end of the needle antenna structure 80 was also modelled. The connection pipes 101,102,103,104 are positioned between the biopsy sample 290 inside the inner conductor 888 and the outside of the outer conductor 85. The connection tubes 101,102,103,104 run through the wall 86 of the inner conductor 88, the first dielectric insulator 87, and the wall of the outer conductor 85. There is a very close proximity between these parts, so it is expected that no extra wall will be required to prevent leakage of the biopsy sample 290 between them, particularly as this is intended that the tri-functional needle antenna is a single use disposable instrument.

Figure 17:
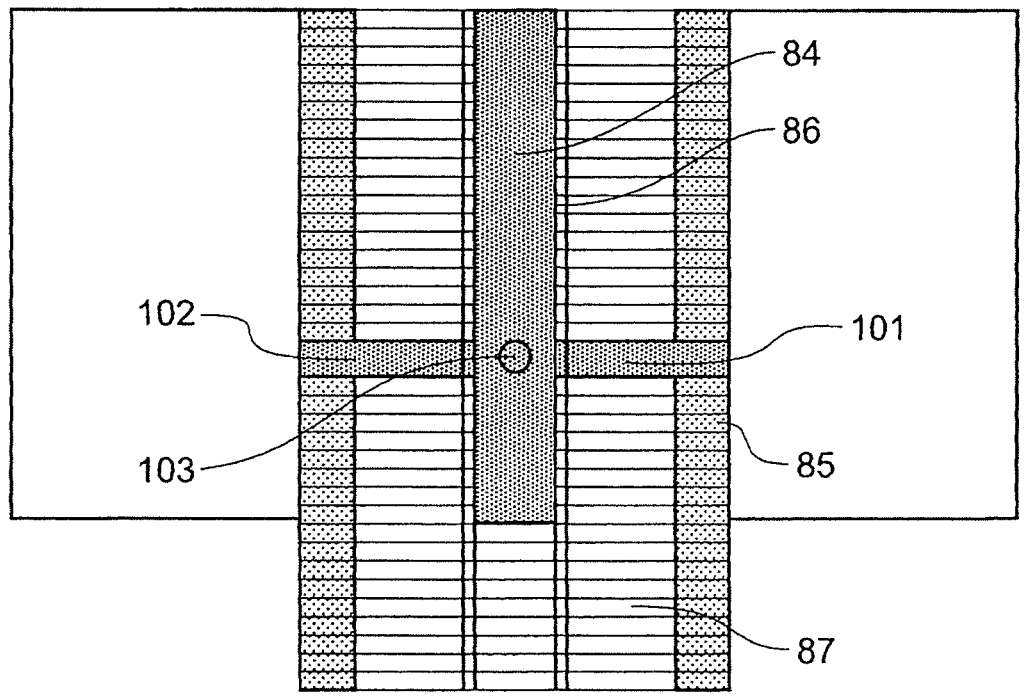
FIG. 17 shows connection pipes for a central biopsy channel in a needle antenna.

The first simulations performed used a configuration where four connection pipes of 0.2 mm diameter were positioned at the same distance from the proximal end of the needle antenna, forming a right-angled cross. The total cross-section of the four connection pipes 101,102,103,104 was equal to the cross-section of the channel 84 inside the inner conductor 88 of the co-axial arrangement. A cross-section through the co-axial needle antenna is shown in FIG. 17. Three of the connection pipes 101,102,103 can be seen. The biopsy sample 290 would be gathered from the four holes in the outer conductor 85 of the coaxial line by an exterior sleeve (or feed pipe 100), which has not been modelled here, as it does not affect microwave performance.

Figure 18:
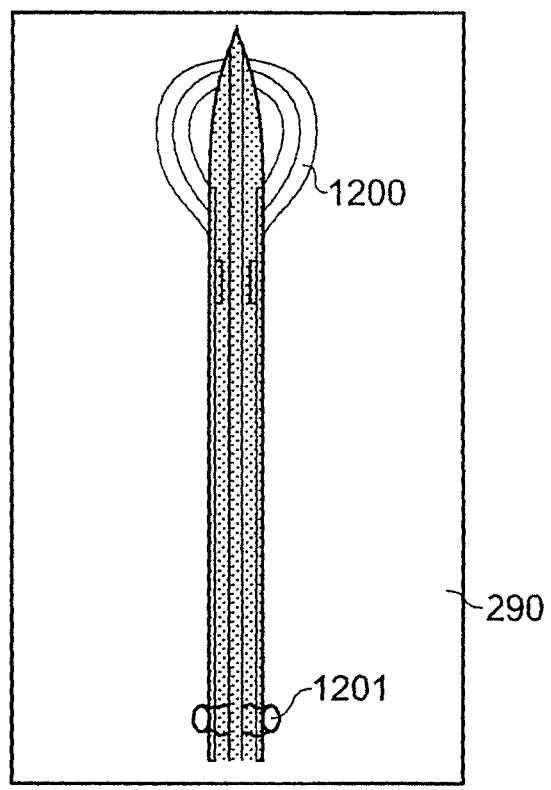
FIG. 18 shows the energy density distribution for a needle antenna with the connection pipes shown in FIG. 17.
Figure 19:
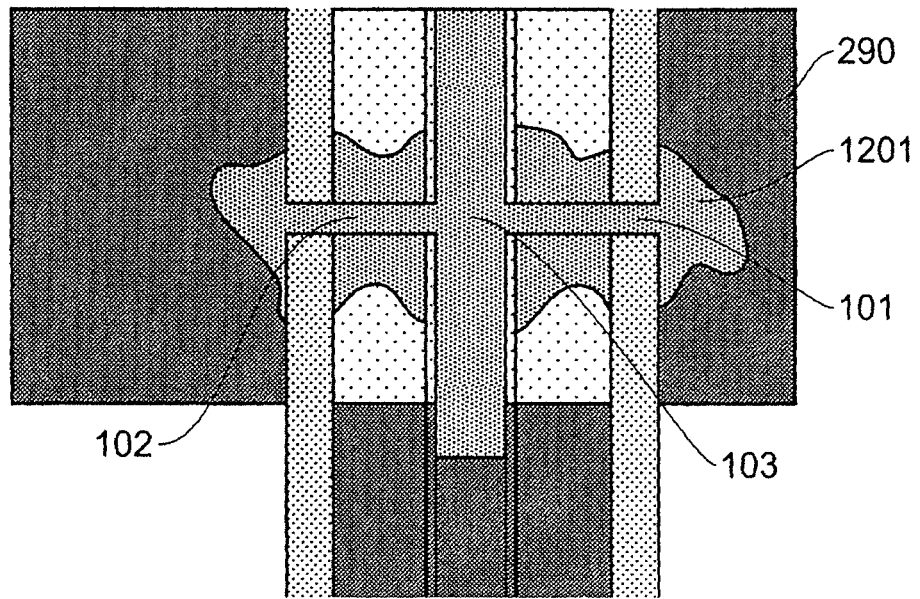
FIG. 19 is a close up view of the energy distribution around the connection pipes shown in FIG. 17.

The power loss density or energy density 1200 in the whole needle antenna structure 80 is shown in FIG. 18, and a magnified picture of the fields at the base, are shown in FIG. 19.

It can be seen that the introduction of the four connection pipes 101,102,103,104, with tumour 290 inside, taken from the biopsy sample, has reduced the total power delivered to the tumour. It is expected that this is due to a combination of impedance mismatch at the connection pipes 101,102,103, 104 and the loss in the pipes. The magnified picture shown in FIG. 19 confirms that there is significant power loss density in and around connection pipes 101,102,103,104.

Figure 20:
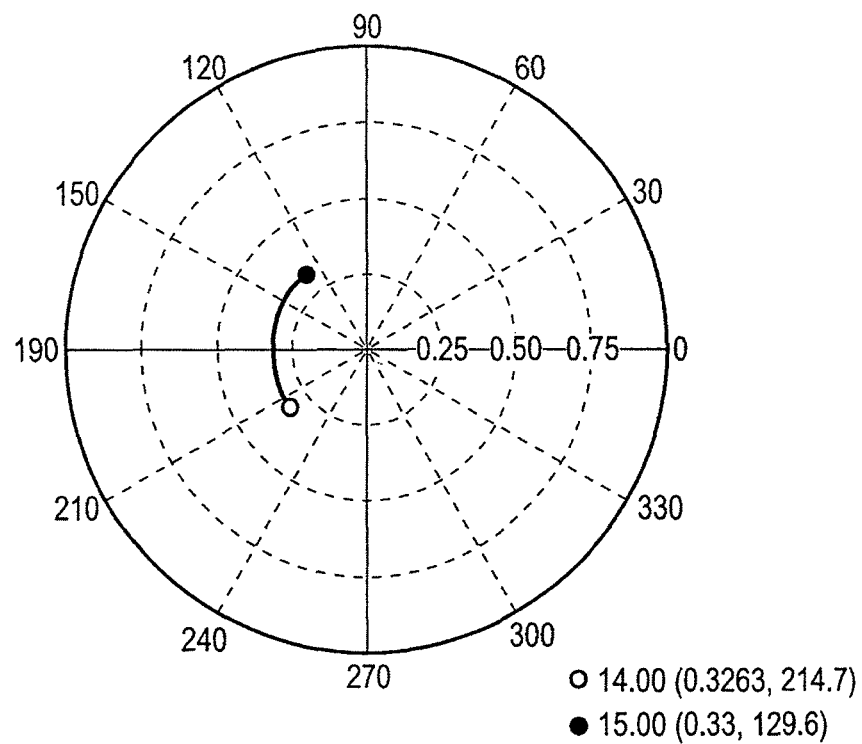
FIG. 20 is a diagram illustrating the impedance match of four equally spaced connecting pipes.

The impedance match to the needle antenna structure 80 for the four connection tubes 101,102,103,104 connected at the same point is shown in FIG. 20.

The arrangement of the holes between the inner and outer conductors 88 and 85 respectively was then modified in order to try to reduce the impedance mismatch and/or loss caused by the holes. Instead of placing the four holes the same distance from the distal tip, at 90 degree spacing around the axis, they were arranged as two in-line pairs, spaced 180 degrees around the axis.

Figure 21:
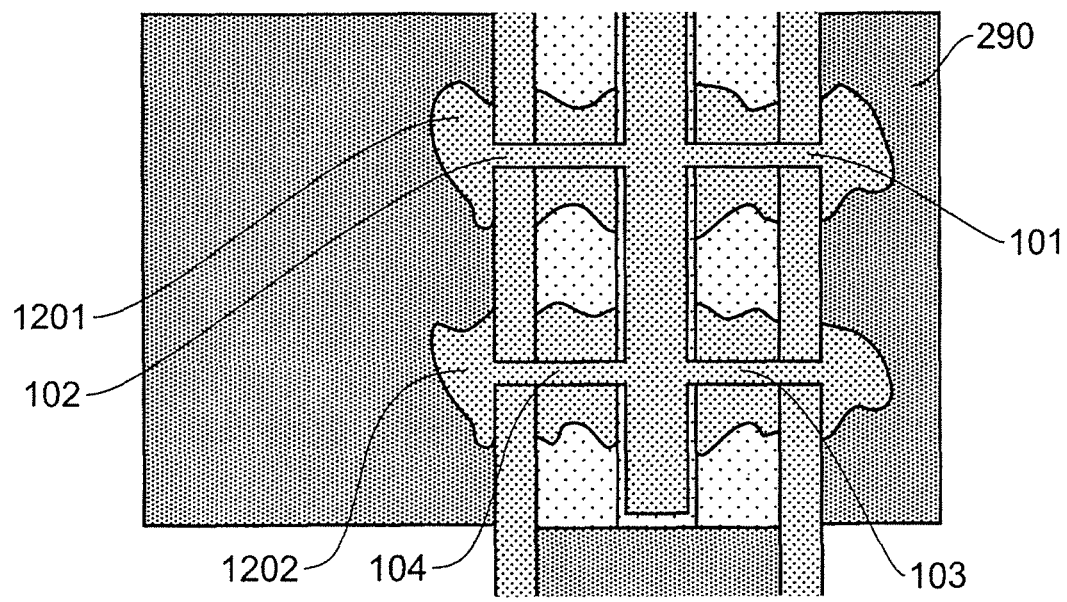
FIG. 21 shows the energy density distribution for a configuration of four connection pipes.
Figure 22:
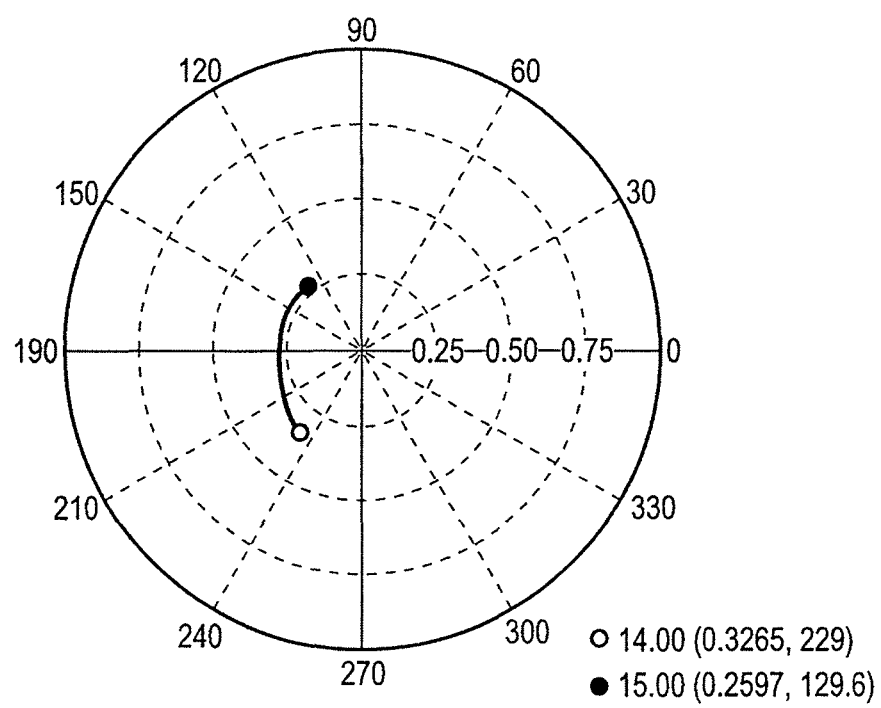
FIG. 22 is a diagram illustrating the impedance match of the four connecting pipes shown in FIG. 21.

Several arrangements were tried, starting with a quarter wavelength separation, i.e. 3.5 mm, which is the ideal separation to give cancellation of two simple identical lossless mismatches. Quarter wavelength proved to give no improvement, so the separation was then reduced, first to 2 mm and then 1.5 mm. The power loss density around the four holes and the match are shown in FIGS. 21 and 22. Although there is no apparent reduction in the loss density around the holes in FIG. 21, it is clear from FIG. 22 that the mismatch has been reduced. This should result in an overall improvement in performance compared to having all the holes at the same distance from the probe tip.

The simulation results show that the needle antenna structure 80 may be modified to introduce a biopsy channel 84 with a 0.4 mm diameter, with either a ceramic or a metal tube, without significantly degrading the controlled ablation, and dielectric measurement features which form an integral part of the current invention.

It is preferable to make the connection to the biopsy channel 84 from the outside of the needle antenna structure 80 using four 0.2 mm diameter holes passing through the inner and outer conductor walls 86 and 85 respectively, and through the intervening first dielectric 87.

The presence of biopsy sample material 290 may result in a small, but acceptable, reduction in the overall performance of the tri-functional needle antenna described in the current invention.

The invention claimed is:

1. Surgical apparatus for introducing material through a needle into biological tissue, the apparatus comprising:
   a power source for delivering microwave energy,
   a needle that is insertable into biological tissue, the needle having:
   an elongate body terminating at a distal end with an insertion tip and at a proximal end with a microwave connector;
   a coaxial cable connected between the power source and the microwave connector;
   a longitudinal channel formed within the elongate body for transporting material to or from the tissue, wherein the longitudinal channel extends through the insertion tip and terminates at an opening in the insertion tip; and
   a coaxial antenna comprising an inner conductor along an inside wall of the longitudinal channel and an outer conductor coaxial with the inner conductor and separated from it by a first dielectric material,
   wherein the insertion tip is made from a second dielectric material and is arranged to create a matched condition between the first dielectric material and a representative tissue impedance for the microwave energy;
   wherein the needle is connected to the power source via a first signal path and a second signal path to receive energy from the power source, and the coaxial antenna is connected to couple the received energy into biological tissue at the insertion tip, and
   wherein the energy delivered on the first signal path has a first frequency and the energy delivered on the second signal path has a second frequency greater than the first frequency.

2. Surgical apparatus according to claim 1, wherein the inner conductor is a conductive tube having a diameter of about 0.5 mm and a wall thickness of about 0.01 mm.

3. Surgical apparatus according to claim 1, wherein the insertion tip comprises a rigid element attached to the first dielectric material of the coaxial antenna, the rigid element extending away from the outer conductor at a distal end of the elongate body.

4. Surgical apparatus according to claim 1, wherein the needle is insertable through any one of an endoscope, a bronchoscope and a cystoscope.

5. Surgical apparatus according to claim 1 including a controller arranged to control the amount of energy delivered into the biological tissue.

6. Surgical apparatus according to claim 1, wherein the needle is arranged to convey a material through the longitudinal channel to react with the energy delivered from the coaxial antenna.

7. Surgical apparatus according to claim 1, wherein the needle is arranged to convey a radioactive implant through the longitudinal channel.

* * * * *